(12) United States Patent
Conner et al.

(10) Patent No.: US 6,506,565 B1
(45) Date of Patent: Jan. 14, 2003

(54) PLANT REGULATORY SEQUENCES FOR SELECTIVE CONTROL OF GENE EXPRESSION

(75) Inventors: Timothy W. Conner, Wildwood, MO (US); Iris Tzafrir, Stillwater, OK (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/651,169

(22) Filed: Aug. 30, 2000

Related U.S. Application Data

(60) Provisional application No. 60/151,892, filed on Sep. 1, 1999.

(51) Int. Cl.$^7$ .................................................. C12Q 1/68
(52) U.S. Cl. .................. 435/6; 435/24.1; 435/69.1; 435/320.1; 435/419; 435/468; 435/412; 800/287; 800/278; 800/281; 800/320.1; 800/320.2; 800/320.3; 536/23.1; 536/23.2; 536/23.6; 536/24.1
(58) Field of Search .................... 435/24.1, 6, 69.1, 435/320.1, 419, 468, 412; 800/287, 278, 281, 320, 320.1, 320.2, 320.3; 536/23.1, 23.2, 24.1, 23.6

(56) References Cited

U.S. PATENT DOCUMENTS 6,225,529 B1 * 5/2001 Lappegard et al. ......... 800/287

OTHER PUBLICATIONS

Genbank Accession No. AW258129, AW244947, AW066391, and AW225244, Mar. 2000.*

NCBI database, National Center for Biotechnology Information, National Library of Medicine, NIH (Bethesda, MD, USA) Accessio.*

Genbank Accession No. AW744780, Jul. 2000.*

Shen, Bo et al., Partial sequencing and mapping of clones from two maize cdna . . . (1994), Plant Molecular Biology 26, pp. 1084–1101.*

Genbank, Accession AW 225244, Walbot, V.*

* cited by examiner

*Primary Examiner*—W. Gary Jones
*Assistant Examiner*—Janell E. Taylor
(74) *Attorney, Agent, or Firm*—Brian K. Stierwalt; Howrey Simon Arnold & White, LLP

(57) ABSTRACT

The present invention relates to nucleic acid sequences for regulating gene expression in plants. In particular, the invention relates to 5' regulatory sequences which are useful for regulating expression of heterologous DNAs in plants and methods for identifying multiple 5' regulatory sequences which confer a particular expression profile when operably linked to DNA sequences. The invention also relates to expression vectors containing the 5' regulatory sequences and to transgenic plants containing the expression vectors.

17 Claims, 8 Drawing Sheets

PLANT REGULATORY SEQUENCES FOR SELECTIVE CONTROL OF GENE EXPRESSION

The present application claims priority of U.S. Provisional Application Ser. No. 60/151,892, filed on Sep. 1, 1999, the entire contents of which is incorporated herein by reference.

FIELD OF THE INVENTION

The present invention relates to the isolation and use of nucleic acid molecules for control of gene expression in plants, specifically novel plant promoters.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al. (1995) World Journal of Microbiology and Biotechnology 11:449–460). Particularly desirable traits or qualities of interest for plant genetic engineering would include but are not limited to resistance to insects and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Since the promoter is a 5' regulatory element which plays an integral part in the overall expression of a gene or gene(s), it would be advantageous to have a variety of promoters to tailor gene expression such that a gene or gene(s) is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, also known as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing which can be caused by recombination of homologous sequences. In light of these and other considerations, it is apparent that optimal control of gene expression and regulatory element diversity are important in plant biotechnology.

The proper regulatory sequences must be present and in the proper location with respect to the DNA sequence of interest, for the newly inserted DNA to be transcribed and thereby, if desired translated into a protein in the plant cell. These regulatory sequences include but are not limited to a promoter, a 5' untranslated leader, and a 3' polyadenylation sequence. The ability to select the tissues in which to transcribe such foreign DNA and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include but are not limited to inducible promoters which can be triggered by external stimuli such as chemical agents, developmental stimuli, or environmental stimuli. Thus, the different types of promoters desired can be obtained by isolating the upstream 5' regulatory regions of DNA sequences which are transcribed and expressed in a constitutive, tissue-enhanced, or inducible manner.

The technological advances of high-throughput sequencing and bioinformatics has provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced and the expressed sequences catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue enhanced sequence can then be used as a probe or primer to clone the corresponding full-length cDNA. A genomic library of the target plant can then be used to isolate the corresponding gene and the associated regulatory elements, including promoter sequences.

Multiple promoter sequences which confer a desired expression profile such as embryogenic or callus tissue-enhanced or specific promoters can be isolated by selectively comparing cDNA target embryogenic tissue or callus tissue libraries with non-target or non-target or background cDNA libraries such as libraries from leaf and root tissue to find the 5' regulatory regions associated with the expressed sequences in those target libraries. The isolated promoter sequences can be used for selectively modulating expression of any operatively linked gene and provide additional regulatory element diversity in a plant expression vector in gene stacking approaches.

SUMMARY OF THE INVENTION

The present invention provides nucleic acid sequences which comprise regulatory sequences located upstream of the 5' end of plant DNA structural coding sequences that are transcribed in embryogenic or callus tissue and shown in SEQ ID NOS: 36–51.

In one aspect, the present invention provides nucleic acid sequences comprising a sequence selected from the group consisting of SEQ ID NOS: 36–51 or any fragments, regions, or cis elements of the sequence which are capable of regulating transcription of operably linked DNA sequences.

The present invention also provides nucleic acid sequences comprising a sequence selected from the group consisting of SEQ ID NOS: 36–51 which are promoters.

Another aspect of the present invention relates to the-use of at least one cis element, or fragment or region thereof of the disclosed 5' promoter sequences which can be combined to create novel promoters or used in a novel combination with another heterologous regulatory sequence to create a chimeric promoter capable of modulating transcription of an operably linked DNA sequence.

Hence, the present invention relates to the use of nucleic acid sequences disclosed in SEQ ID NOS: 36–51, or any fragment, region, or cis elements of the disclosed sequences which are capable of regulating transcription of a DNA sequence when operably linked to the DNA sequence. Therefore, the invention not only encompasses the sequences as disclosed in SEQ ID NOS: 36–51 but also includes any truncated or deletion derivatives, or fragments or regions thereof which are capable of functioning independently as promoters, including cis elements which are capable of functioning as regulatory sequences in conjuction with one or more regulatory sequences when operably linked to a transcribable sequence.

The present invention thus encompasses a novel promoter, or a chimeric or hybrid promoter comprising a nucleic acid sequence as disclosed in SEQ ID NOS: 36–51. The chimeric or hybrid promoters can consist of any length fragments, regions, or cis elements of the disclosed sequences of SEQ ID NOS: 36–51 combined with any other transcriptionally active minimal or full-length promoter. For example, a promoter sequence selected from SEQ ID NOS: 36–51 can be combined with a CaMV 35S or other promoter to construct a novel chimeric promoter. A minimal promoter can also be used in combination with the nucleic acid sequences of the present invention. A novel promoter also comprises any promoter constructed by engineering the nucleic acid sequences disclosed in SEQ ID NOS: 36–51 or any fragment, region, or cis element of the disclosed sequences in any manner sufficient to transcribe an operably linked DNA sequence.

Another aspect of the present invention relates to the ability of the promoter sequences of SEQ ID NOS: 36–51, or fragments, regions, or cis elements thereof to regulate transcription of operably linked transcribably sequences in embryogenic or callus tissues. Fragments, regions, or cis elements of SEQ ID NOS: 36–51 which are capable of regulating transcription of operably linked DNA sequences in certain tissues can be isolated from the disclosed nucleic acid sequences of SEQ ID NOS: 36–51 and used to engineer novel promoters which confer embryogenic-enhanced or callus-enhanced expression of operably linked DNA sequences or in combinations with other heterologous regulatory sequences.

The present invention also encompasses DNA constructs-comprising the disclosed is sequences as shown in SEQ ID NOS: 36–51 or any fragments, regions, or cis elements thereof, including novel promoters generated using the disclosed sequences or any fragment, region, or cis element of the disclosed sequences.

The present invention also includes any cells and transgenic plants containing the DNA disclosed in the sequences as shown in SEQ ID NOS: 36–51 or any fragments, regions, or cis elements thereof.

The present invention also provides a method of regulating transcription of a DNA sequence comprising operably linking the DNA sequence to any nucleic acid comprising all or any fragment, region or cis element of a sequence selected from the group consisting of SEQ ID NOS: 36–51.

In a another embodiment the present invention provides a method of conferring embryogenic or callus tissue-enhanced or specific expression by operably linking a sequence selected from the group consisting of SEQ ID NOS: 36–51, or any fragment, region, or cis element of the disclosed sequences to any transcribable DNA sequence. The fragments, regions, or cis elements of the disclosed promoters as shown in SEQ ID NOS: 36–51 which are capable of conferring enhanced expression in embryogenic or callus tissues to operably linked DNA sequences can be engineered and used independently in novel combinations including multimers, or truncated derivatives and the novel promoters can be operably linked with a transcribable DNA sequence. The disclosed fragments, regions, or cis elements of the disclosed sequences which are capable of conferring enhanced expression in embryogenic or callus tissues to operably linked DNA sequences can be used in combination with a heterologous promoter including a minimal promoter to create a novel chimeric or hybrid promoter.

The present invention also provides a method of making a transgenic plant by introducing into the cell of a plant a DNA construct comprising: (i) a promoter comprising a nucleic acid comprising a sequence selected from the group consisting of SEQ ID NOS: 36–51, or fragments, regions, or cis elements thereof, and operably linked to the promoter, (ii) a transcribable DNA sequence and (iii) a 3' untranslated region.

The present invention also provides a method of isolating at least one 5' regulatory sequence of a desired expression profile from a target plant of interest by evaluating a collection of nucleic acid sequences of ESTs derived from at least one cDNA library prepared from a plant cell type of interest, comparing EST sequences from at least one target plant cDNA library and at least one non-target cDNA library of ESTs from a different plant cell type, subtracting common EST sequences found in both target and non-target libraries, designing gene-specific primers from the remaining ESTs after the subtractions which are representative of the targeted expressed sequences, and isolating at least one corresponding 5' flanking and regulatory sequence, which includes at least one promoter sequence from a genomic library prepared from the target plant using the gene specific primers.

The foregoing and other aspects of the invention will become more apparent from the following detailed description and accompanying drawings.

Figure 1:
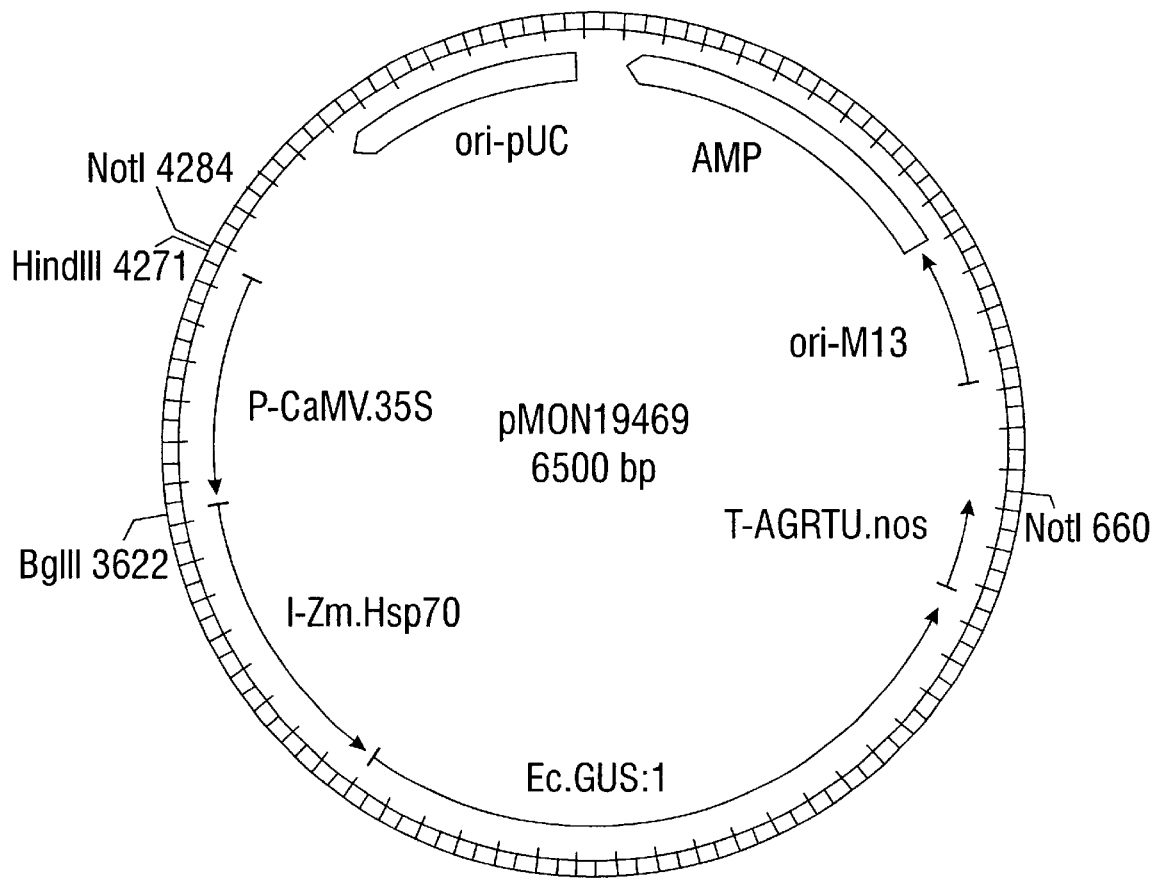
FIG. 1 is a plasmid map of pMON19469

Plasmid pMON19469 is an expression vector consisting of the following genetic components: P-CaMV.35S is the promoter for the 35S RNA from CaMV containing a tandem duplication of the −90 to −300 region (U.S. Pat. No. 5,322,938 herein incorporated by reference in their entirety); I-Zm.Hsp70 intron is the intervening sequence of the maize heat shock protein as described in U.S. Pat. Nos. 5,593,874 and 5,859,347 herein incorporated by reference in their entirety); Ec.GUS:1 is the coding region for beta-glucuronidase from *E. coli*; T-AGRTU.nos is the termination signal from the nopaline synthase gene; ori-M13 and ori-pUC are origins of replication; AMP is the coding region for ampicillin selection.

Plasmid pMON39721 is a double border (right (RB) and left (LB) T-DNA borders) plant transformation vector consisting of the following genetic components: P-CaMV.35S is the CaMV 35S promoter (U.S. Pat. No. 5,352,605 herein incorporated by reference in their entirety); AGRTU.nptII is the coding sequence from *Agrobacterium tumefaciens* that confers resistance to kanamycin antibiotic; T-AGRTU.nos is the 3' termination sequence of the nopaline synthase gene isolated from *Agrobacterim tumefaciens*; ori322 and oriV are origins of replication; aad is the coding sequence that confers resistance to spectinomycin and streptomycin antibiotics.

Plasmid pMON51002 is an expression vector consisting of the following genetic components: ZM-70025861 is the promoter for the *Zea mays* embryo enhanced expression isolated from a *Zea mays* embryo genomic library; I-Zm.Hsp70 intron is the intervening sequence of the maize heat shock protein as described in U.S. Pat. Nos. 5,593,874 and 5,859,347 herein incorporated by reference in their entirety; Ec.GUS:1 is the coding region for beta-glucuronidase from *E. coli*; T-AGRTU.nos is the termination signal from the nopaline synthase gene; ori-M13 and ori-pUC are origins of replication; AMP is the coding region for ampicillin selection.

Plasmid pMON51008 is a double border, right (RB) and left (LB) T-DNA borders, plant transformation vector consisting of the following genetic components: ZM-70025861 is the promoter for the *Zea mays* embryo enhanced expression isolated from a *Zea mays* embryo genomic library; I-Zm.Hsp70 intron is the intervening sequence of the maize heat shock protein as described in U.S. Pat. Nos. 5,593,874 and 5,859,347 herein incorporated by reference in their entirety); Ec.GUS:1 is the coding region for beta-glucuronidase from *E. coli*; TAGRTU.nos is the termination signal from the nopaline synthase; P-CaMV.35S is the CaMV 35S promoter (U.S. Pat. No. 5,352,605 herein incorporated by reference in their entirety); AGRTU.nptII is the coding sequence from *Agrobacterium tumefaciens* that confers resistance to kanamycin antibiotic; T-AGRTU.nos is the 3' termination sequence of the nopaline synthase gene isolated from *Agrobacterim tumefaciens*; ori322 and oriV are origins of replication; aad is the coding sequence that confers resistance to spectinomycin and streptomycin antibiotics.

Plasmid pMON51001 is an expression vector consisting of the following genetic components: ZM-700267629 is the promoter for the *Zea mays* embryo enhanced expression isolated from a *Zea mays* embryo genomic library; I-Zm.Hsp70 intron is the intervening sequence of the maize heat shock protein as described in U.S. Pat. Nos. 5,593,874 and 5,859,347 herein incorporated by reference in their entirety; Ec.GUS:1 is the coding region for beta-glucuronidase from *E coli*; T-AGRTU.nos is the termination signal from the nopaline synthase gene; ori-M13 and ori-pUC are origins of replication; AMP is the coding region for ampicillin selection.

Plasmid pMON51009 is a double border, right (RB) and left (LB) T-DNA borders, plant transformation vector consisting of the following genetic components: ZM-700267629 is the promoter for the *Zea mays* embryo enhanced expression isolated from a *Zea mays* embryo genomic library; I-Zm.Hsp70 intron is the intervening sequence of the maize heat shock protein as described in U.S. Pat. Nos. 5,593,874 and 5,859,347 herein incorporated by reference in their entirety); Ec.GUS:1 is the coding region for beta-glucuronidase from *E. coli*; TAGRTU.nos is the termination signal from the nopaline synthase gene, P-CaMV.35S is the CaMV 35S promoter (U.S. Pat. No. 5,352,605 herein incorporated by reference in their entirety); AGRTU.nptII is the coding sequence from *Agrobacterium tumefaciens* that confers resistance to kanamycin antibiotic; T-AGRTU.nos is the 3' termination sequence of the nopaline synthase gene isolated from *Agrobacterim tumefaciens*; ori322 and oriV are origins of replication; aad is the coding sequence that confers resistance to spectinomycin and streptomycin antibiotics.

Plasmid pMON51003 is an expression vector consisting of the following genetic components: ZM-700263624 is the promoter for the *Zea mays* embryo enhanced expression isolated from a *Zea mays* embryo genomic library; I-Zm.Hsp70 intron is the intervening sequence of the maize heat shock protein as described in U.S. Pat. Nos. 5,593,874 and 5,859,347 herein incorporated by reference in their entirety); Ec.GUS:1 is the coding region for beta-glucuronidase from *E. coli*; T-AGRTU.nos is the termination signal from the nopaline synthase gene; ori-M13 and ori-pUC are origins of replication; AMP is the coding region for ampicillin selection.

Plasmid pMON51010 is a double border, right (RB) and left (LB) T-DNA borders, plant transformation vector consisting of the following genetic components: ZM-700263624 is the promoter for the *Zea mays* embryo enhanced expression isolated from a *Zea mays* embryo genomic library; I-Zm.Hsp70 intron is the intervening sequence of the maize heat shock protein described in U.S. Pat. Nos. 5,593,874 and 5,859,347 herein incorporated by reference in their entirety); Ec.GUS:1 is the coding region for beta-glucuronidase from *E. coli*; TAGRTU.nos is the termination signal from the nopaline synthase gene, P-CaMV.35S is the CaMV 35S promoter (U.S. Pat. No. 5,352,605 herein incorporated by reference in their entirety) AGRTU.nptII is the coding sequence from *Agrobacterium tumefaciens* that confers resistance to kanamycin antibiotic; T-AGRTU.nos is the 3' termination sequence of the nopaline synthase gene isolated from *Agrobacterim tumefaciens*; ori322 and oriV are origins of replication; aad is the coding sequence that confers resistance to spectinomycin and streptomycin antibiotics.

DETAILED DESCRIPTION OF THE INVENTION

This application claims the benefit of U.S. Provisional Application No. 60/151,892, filed Sep. 1, 1999.

Genes of interest (GOI) conferring tolerance to an herbicide or antibiotic, insecticidal protein gene, disease resistance genes, genes that affect plant growth, metabolism or development, oil production and modified oils and genes encoding pharmaceutical proteins, for example, are considered as aspects of the present invention. Such compositions and methods disclosed herein may be used with respect to any plant that can be genetically modified by the methods of plant biotechnology. The compositions and methods herein describe DNA sequences useful for expression of transgene products in plant embryos and plant seeds.

The following definitions and methods are provided to better define the present invention and to guide those of ordinary skill in the art in the practice of the present invention. Unless otherwise noted, terms are to be understood according to conventional usage by those of ordinary skill in the relevant art. The nomenclature for DNA bases as set forth at 37 CFR § 1.822 is used. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source, is modified from its original form.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified, as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantially identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman Adv. Appl. Math. 2:482, 1981; by the homology alignment algorithm of Needleman and Wunsch, J. Mol. Biol. 48:443, 1970; by the search for similarity method of Pearson and Lipman, Proc. Natl. Acad. Sci. USA 85:2444, 1988; preferably by computerized implementations of these algorithms (GAP, BESTFIT, FASTA, and TFASTA in the Wisconsin Genetics Software Package Release 7.0, Genetics Computer Group, 575 Science Dr., Madison, Wis. The reference nucleic acid may be a full-length molecule or a portion of a flonger molecule. Alternatively, two nucleic acids are have substantial: identity if one hybridizes to the other under stringent conditions, as defined below.

A first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., 1989, and Ausubel et al., 1992). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence which is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g. rRNA, tRNA); and other types of gene function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element which may also be a component or part of an expression vector. Examples of genetic components include, but are not limited to promoter regions, 5' untranslated leaders, introns, genes, 3' untranslated regions, and other regulatory sequences or sequences which affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association:of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"ESTs" or Expressed Sequence Tags are short sequences of randomly selected clones from a cDNA (or complementary DNA) library which are representative of the cDNA inserts of these randomly selected clones (McCombie, et al., Nature Genetics, 1:124, 1992; Kurata, et al., Nature Genetics, 8: 365,1994; Okubo, et al., Nature Genetics, 2: 173, 1992).

The term "electronic Northern" refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries.

"Subsetting" refers to a method of comparing nucleic acid sequences from different or multiple sources which can be used to assess the expression profile of the nucleic acid sequences which reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulation expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349–383, 1981; Messing et al., In: Genetic Engineering of Plants, Kosuge et al., eds., pp. 211–227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211–227, 1983). In addition, virtually all promoters include additional upstream activating sequences or enhancers (Benoist and Chambon, nature 290:304–310, 1981; Gruss et al., Proc. Nat. Acad. Sci. USA 78:943–947, 1981; and Khoury and Gruss, Cell 27:313–314, 1983) extending from around −100 bp to −1,000 bp or more upstream of the transcription initiation site.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106–1112, 1986; Ellis et al., EMBO J. 6:11–16, 1987; Strittmatter and Chua, Proc. Nat. Acad. Sci. USA 84:8986–8990, 1987; Poulsen and Chua, Mol. Gen. Genet. 214:16–23, 1988; Comai et al., Plant Mol. Biol. 15:373–381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232:1106–1112, 1986; Strittmatter and Chua, Proc. Nat. Acad. Sci. USA 84:8986–8990, 1987; Aryan et al., Mol. Gen. Genet. 225:65–71, 1991).

Promoters are typically comprised of multiple distinct "cis-acting transcriptional regulatory elements," or simply "cis-elements," each of which can confer a different aspect of the overall control of gene expression (Strittmatter and Chua, Proc. Nat. Acad. Sci. USA 84:8986–8990, 1987; Ellis et al., EMBO J. 6:11–16, 1987; Benfey et al., EMBO J. 9:1677–1684, 1990). "cis elements" bind trans-acting protein factors that regulate transcription. Some cis elements bind more than one factor, and trans-acting transcription factors may interact with different affinities with more than one cis element (Johnson and McKnight, Ann. Rev. Biochem. 58:799–839, 1989). Plant transcription factors, corresponding cis elements, and analysis of their interaction are discussed, for example, in: Martin, Curr. Opinions Biotech. 7:130–138, 1996; Murai, In: Methods in Plant Biochemistry and Molecular Biology, Dashek, ed., CRC Press, 1997, pp. 397–422; and Methods in Plant Molecular Biology, Maliga et al., eds., Cold Spring Harbor Press, 1995, pp. 233–300. The promoter sequences of the present invention can contain "cis elements" which can modulate gene expression.

Cis elements can be identified by a number of techniques, including deletion analysis, i.e., deleting one or more nucleotides from the 5' end or internal to a promoter; DNA binding protein analysis using Dnase I footprinting, methylation interference, electrophoresis mobility shift assays, in vivo genomic footprinting by ligation-mediated PCR, and other conventional assays; or by sequence similarity with known cis element motifs by conventional sequence comparison methods. The fine structure of a cis element can be further studies by mutagenesis (or substitution) of one or more nucleotides or by other conventional methods. See, e.g., Methods in Plant Biochemistry and Molecular Biology, Dashek, ed., CRC Press, 1997, pp. 397–422; and Methods in Plant Molecular Biology, Maliga et al., eds., Cold Spring Harbor Press, 1995, pp. 233–300.

Cis elements can be obtained by chemical synthesis or by cloning from promoters that includes such elements, and they can be synthesized with additional flanking sequences that contain useful restriction enzyme sites to facilitate subsequence manipulation. In one embodiment, the promoters are comprised of multiple distinct "cis-acting transcriptional regulatory elements," or simply "cis-elements," each of which can modulate a different aspect of the overall control of gene expression (Strittmatter and Chua, Proc. Nat. Acad. Sci. USA 84:8986–8990, 1987; Ellis et al., EMBO J. 6:11–16, 1987; Benfey et al., EMBO J. 9:1677–1684, 1990). For example, combinations of cis element regions or fragments of the 35S promoter can show tissue-specific patterns of expression (see U.S. Pat. No. 5,097,025 herein incorporated by reference in its entirety). In one embodiment sequence regions comprising "cis elements" of the nucleic acid sequences of SEQ ID NOS: 36–51 can be identified using computer programs designed specifically to identity cis elements, domains, or motifs within sequences by a comparison with known cis elements or can be used to align multiple 5' regulatory sequences to identify novel cis elements.

The present invention includes cis elements of SEQ ID NOs: 36–51 or homologues of cis elements known to effect gene regulation that show homology with the nucleic acid sequences of the present invention. A number of such elements are known in the literature, such as elements which are regulated by numerous factors such as light, heat, or stress; elements which are regulated or induced by pathogens or chemicals, and the like. Such elements may either positively or negatively regulated gene expression, depending on the conditions. Examples of cis elements would include but are not limited to oxygen responsive elements (Cowen et al., J. Biol. Chem. 268(36):26904, 1993), light regulatory elements (see for example, Bruce and Quaill, Plant Cell 2(11): 1081. 1990, and Bruce et al., EMBO J. 10:3015, 1991, a cis element responsive to methyl jasmonate treatment (Beaudoin and Rothstein, Plant Mol. Biol. 33:835, 1997, salicylic acid responsive elements (Strange et al., Plant J. 11:1315, 1997, heat shock responsive elements (Pelham et al., Trends Genet. 1:31, 1985, elements responsive to wounding and abiotic stress (Loace et al., Proc. Natl. Acad. Sci. U.S.A. 89:9230, 1992; Mhiri et al., Plant Mol. Biol. 33:257, 1997), low temperature elements (Baker et al., Plant Mol. Biol. 24:701, 1994; Jiang et al., Plant Mol. Biol. 30:679, 1996; Nordin et al., Plant Mol. Biol. 21:641, 1993; Zhou et al., J. Biol. Chem. 267:23515, 1992), and drought responsive elements, (Yamaguchi et al., Plant Cell 6:254–264, 1994; Wang et al., Plant Mol. Biol. 28:605, 1995; Bray E. A. Trends in Plant Science 2:48, 1997).

The present invention therefore encompasses regions, domains, fragments or "cis elements" of the disclosed nucleic acid molecules and the nucleic acid fragments can include any contiguous region of the disclosed sequences. The promoter regions of the present invention as shown in SEQ ID NOs: 36–51 can contain one or more regulatory elements including but not limited to "cis elements" or domains which are capable of regulating transcription of operably linked DNA sequences in plant seeds and tissues of the plant seeds. Plant seed tissues include the embryo comprised of embryonic cells and embryo tissues such as the scutellum, the endosperm, the aluerone, and the seed coat.

Plant promoters can include promoters produced through the manipulation of known promoters to produce synthetic, chimeric, or hybrid promoters. Such promoters can combine cis elements from one or more promoters, for example, by adding a heterologous regulatory sequence to an active promoter with its own partial or complete regulatory sequences (Ellis et al., EMBO J. 6:11–16, 1987; Strittmatter and Chua, Proc. Nat. Acad. Sci. USA 84:8986–8990, 1987; Poulsen and Chua, Mol. Gen. Genet. 214:16–23, 1988; Comai et al., Plant. Mol. Biol. 15:373–381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106–1112, 1986; Strittmatter and Chua, Proc. Nat. Acad. Sci. USA 84:8986–8990, 1987; Aryan et al., Mol. Gen. Genet. 225:65–71, 1991). The design, construction, and use of chimeric or hybrid promoters comprising at least one of the cis elements of SEQ ID NOs: 36–51 for modulating the expression of operably linked nucleic acid sequences is thus encompassed by the present invention.

The promoter sequences, fragments, regions or cis elements thereof of SEQ ID NOS: 36–51 are capable of transcribing DNA sequences in embryogenic or callus tissue and therefore can selectively regulate expression of genes in these tissues. Promoter sequences which regulate gene expression preferentially in embryogenic or callus tissues have utilityin transformation and for selective expression of genes in maternal tissues. For example, callus-enhanced or embryo enhanced promoters can be operably linked to scorable markers such as GUS or GFP. These reporter genes code for β-glucuronidase and green fluorescent protein, respectively, and when operably linked to the 5' regulatory sequences of the present invention, can provide an indication of the transformation potential of embryogenic tissues and for optimizing transformation and regeneration parameters. The 5' regulatory sequences of the present invention can also be used for selective transcription of any gene or genes of interest including, but not limited to those a genes for enhancing seed quality traits.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage, or under particular environmental conditions. By identifying differentially expressed genes in plant tissues at different developmental stages, or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis which compares the abundance of expressed genes in one or more libraries. The clones contained within a cDNA library are sequenced and the sequences compared with sequences from publicly available databases. Computer-based methods allows the researcher to provide queries which compare sequences from multiple libraries. The process enables quick identification of clones of interest compared with conventional hybridization subtraction methods known to those of skill in the art.

Using conventional methodologies, cDNA libraries can be constructed from the mRNA (messenger RNA) of a given tissue or organism using poly dT primers and reverse transcriptase (Efstratiadis, et al., Cell 7:279, 1976; Higuchi, et al., Proc. Natl. Acad. Sci. (U.S.A.) 73:3146, 1976; Maniatis, et al., Cell 8:163, 1976; Land et al., Nucleic Acids Res. 9:2251, 1981; Okayama, et al., Mol. Cell. Biol. 2:161, 1982; Gubler, et al., Gene 25:263, 1983).

Several methods can be employed to obtain full-length cDNA constructs. For example, terminal transferase can be used to add homopolymeric tails of dC residues to the free 3' hydroxyl groups (Land, et al., Nucleic Acids Res. 9:2251, 1981). This tail can then be hybridized by a poly dG oligo which can act as a primer for the synthesis of full length second strand cDNA. Okayama and Berg, report a method for obtaining full length cDNA constructs. This method has been simplified by using synthetic primer-adapters that have both homopolymeric tails for priming the synthesis of the first and second strands and restriction sites for cloning into plasmids (Coleclough, et al., Gene 34:305, 1985) and bacteriophage vectors (Krawinkel, et al., Nucleic Acids Res. 14:1913, 1986; and Han, et al., Nucleic Acids Res. 15:6304, 1987).

These strategies can be coupled with additional strategies for isolating rare mRNA populations. For example, a typical mammalian cell contains between 10,000 and 30,000 different mRNA sequences. Davidson, Gene Activity in Early Development, 2nd ed., Academic Press, New York, 1976. The number of clones required to achieve a given probability that a low-abundance mRNA will be present in a cDNA library is $N =(ln(1-P))/(ln(1-1/n))$ where N is the number of clones required, P is the probability desired, and 1/n is the fractional proportion of the total mRNA that is represented by a single rare mRNA (Sambrook, et al., 1989).

One method to enrich preparations of mRNA for sequences of interest is to fractionate by size. One such method is to fractionate by electrophoresis through an agarose gel (Pennica, et al., Nature 301:214, 1983). Another such method employs sucrose gradient centrifugation in the presence of an agent, such as methylmercuric hydroxide, that denatures secondary structure in RNA (Schweinfest, et al., Proc. Natl. Acad. Sci. (U.S.A.) 79:4997–5000, 1982).

A frequently adopted method is to construct equalized or normalized cDNA libraries (Ko, Nucleic Acids Res. 18:5705, 1990; Patanjali, S. R. et al., Proc. Natl. Acad. Sci. (U.S.A.) 88:1943, 1991). Typically, the cDNA population is normalized by subtractive hybridization. Schmid, et al., J. Neurochem. 48:307, 1987; Fargnoli, et al., Anal. Biochem. 187:364, 1990; Travis, et al., Proc. Natl. Acad. Sci (U.S.A.) 85:1696, 1988; Kato, Eur. J. Neurosci. 2:704, 1990; and Schweinfest, et al., Genet. Anal. Tech. Appl. 7:64, 1990). Subtraction represents another method for reducing the population of certain sequences in the cDNA library. Swaroop, et al., Nucleic Acids Res. 19:1954, 1991). Normalized libraries can be constructed using the Soares procedure (Soares et al., Proc. Natl. Acad. Sci. (U.S.A.) 91:9228, 1994). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected, and clones for rare transcripts are effectively increased in abundance.

ESTs can be sequenced by a number of methods. Two basic methods can be used for DNA sequencing, the chain termination method of Sanger et al., Proc. Natl. Acad. Sci. (U.S.A.) 74: 5463, 1977 and the chemical degradation method of Maxam and Gilbert, Proc. Nat. Acad. Sci. (U.S.A.) 74: 560, 1977. Automation and advances in technology such as the replacement of radioisotopes with fluorescence-based sequencing have reduced the effort required to sequence DNA (Craxton, Methods, 2: 20, 1991; Ju et al., Proc. Natl. Acad. Sci. (U.S.A.) 92: 4347, 1995; Tabor and Richardson, Proc. Natl. Acad. Sci. (U.S.A.) 92: 6339, 1995). Automated sequencers are available from a number of manufacturers, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

ESTs longer than 150 bp have been found to be useful for similarity searches and mapping. (Adams, et al., Science 252:1651, 1991. EST sequences normally range from 150–450 bases. This is the length of sequence information that is routinely and reliably generated using single run sequence data. Typically, only single run sequence data is obtained from the cDNA library, Adams, et al., Science 252:1651, 1991. Automated single run sequencing typically results in an approximately 2–3% error or base ambiguity rate. (Boguski, et al., Nature Genetics, 4:332, 1993).

EST databases have been constructed or partially constructed from, for example, C. elegans (McCombrie, et al., Nature Genetics 1:124, 1992, human liver cell line HepG2 (Okubo, et al., Nature Genetics 2:173, 1992); human brain RNA (Adams, et al., Science 252:1651, 1991; Adams, et al., Nature 355:632, 1992); *Arabidopsis*, (Newman, et al., Plant Physiol. 106:1241, 1994):c;,and rice (Kurata, et al., Nature Genetics 8:365, 1994). The present invention uses ESTs isolated from a number of libraries prepared from corn embryogenic and callus tissue as a tool for the identification of promoter sequences associated with genes expressed in these desired tissues which then faciliatates the isolation of 5' regulatory sequences such as promoters which regulate the genes.

Computer-based sequence analyses can be used to identify differentially expressed sequences including but not limited to those sequences expressed in one tissue compared with another tissue. For example, a different set of sequences can be found from cDNA isolated from plant tissue isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library, or a collection of cDNA libraries. For example, the identification of regulatory sequences that regulate the expression of transcripts in embryogenic or callus tissue is conducted by identifying ESTs found in cDNA libraries prepared from embryogenic or callus tissue and absent or in lower abundance in other cDNA libraries in the database. The identified EST leads are then evaluated for relative abundance within the library and the expression profile for a given EST is assessed. By abundance as used herein is meant the number of times a clone or cluster of clones appears in a library. The sequences that are enhanced or in high abundance in a specific tissue or organ which represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not limited to inverse PCR (IPCR), vectorette PCR, Y-shaped PCR and genome walking approaches.

In a preferred embodiment, genomic DNA ligated to an adaptor is subjected to a primary round of PCR amplification with a gene-specific primer and a primer which anneals to the adaptor sequence. The PCR product is next used as the template for a nested round of PCR amplification with a second gene-specific primer and second adaptor. The resulting fragments from the nested PCR reaction are then isolated, purified and subcloned into an appropriate vector. The fragments are sequenced and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses and subsequently the 5' regulatory regions are operably linked to other genes and regulatory sequences of interest in a suitable plant transformation vector and the transformed plants are analyzed for the expression of the gene(s) of interest by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, Arabidopsis, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plant targets would include corn, cotton, soybean, and wheat.

The nucleic acid molecules of the present invention are isolated from corn (*Zea mays*). The corn plant develops about 20–21 leaves, silks about 65 days post-emergence, and matures about 125 days post-emergence. Normal corn plants follow a general pattern of development, but the time interval between different stages and morphology varies between different hybrids, growth and environmental conditions.

There are a number of identifiable stages in corn plant development. The stages are defined as vegetative (V) and reproductive (R) stages. Subdivisions of the V stages are numerically designated as V1, V2, V3, etc., through V(n) where (n) represents the last leaf stage before tasseling (VT) and the first V stage is the emergence (VE) stage. For example, VE is the emergence from the soil of a seedling leaf, V1 represents the first true leaf, V2 represents the second leaf, etc. The reproductive stages include the first appearance of silk to the mature seed and are represented as follows: R1 is silking, R2 is blistering, R3 is the milk stage, R4 is the dough stage, R5 is the dent stage, and R6 is physiological maturity (see for example, Ritchie SW et al. (1986) *How a Corn Plant Develops*, Iowa State University of Science and Technology Cooperative Exension Service, Ames, Iowa 48: 1–21).

Any type of plant tissue can be used as a target tissue for the identification of genes and associated regulatory sequences including but not limited to promoter sequences. For the present invention corn tissue is used. More preferably corn embryogenic or corn callus tissues are the target tissues for identification of promoter sequences. Corn cDNA libraries are constructed from embryo tissue isolated from corn twenty-one days after pollination (21-DAP) and thirteen days after pollination (13-DAP), and TypeII corn callus tissue.

Any method which allows a differential comparison between different types or classes of sequences can be used to isolate genes or regulatory sequences of interest. For example in one differential screening approach, a cDNA library from mRNA from a particular tissue can be prepared in a bacteriophage host using a commercially available cloning kit. The plaques are spread onto plates containing lawns of a bacteria host such as *E. coli* to generate bacteriophage plaques. About $10^5$–$10^6$ plaques can be lifted only DNA binding membranes. Duplicate membranes are probed using probes generated from mRNA from the target and non-target tissues to determine differential expression between the target tissue and a non-target or background tissue. The probes are labeled to facilitate detection after hybridization and development. Plaques which hybridize to target tissue-derived probes but.not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage, and prepared using a suitable kit as described earlier (see for example Stratagene, La Jolla, Calif. or Gibco BRL Gaithersburg, Md.).

Differential hybridization techniques as described are well known to those of skill in the art and can be used to isolated a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types. The disclosed method provides an example of a differential screening approach based on electronic sequence analyses of plant ESTs derived from diverse cDNA libraries.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to a -multiple of labeled cDNA probes prepared from RNA samples of different cell or tissue types, allowing direct comparative analysis of expression. This technology was first demonstrated by analyzing 48 Arabidopsis genes for differential expression in roots and shoots (Schena et al, Science, 270:467, 1995). More recently, the expression profiles of over 1400 genes were monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be undertaken by determining the similarity of the test or query sequence with sequences in publicly available or proprietary databases ("similarity analysis") or by searching for certain motifs ("intrinsic sequence analysis") (e.g. cis elements) (Coulson, Trends in Biotechnology, 12:76, 1994; Birren, et al., Genome Analysis, 1:543, 1997).

The nucleotide sequences provided in SEQ ID NOs:36–51 or fragments thereof, or complements thereof, or a nucleotide sequence at least 90% identical, preferably 95% identical even more preferably 99% or 100% identical to the sequence provided in SEQ ID NOs: 36–51 or fragment thereof, or complement thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Sequences can be analyzed by a number of methods such as by analyzing the sequences without the aid of software designed for such purposes. Computer software is also publicly available which allows one of skill in the art to access sequence information provided in a computer readable medium. Examples of public databases would include but is not limited to the DNA Database of Japan (DDBJ) (http://www.ddbj.nig.ac.jp/);Genebank (http:/Hwww.ncbi.nlm.nih.gov/web/Genbank/Index.html); and the European Molecular Biology Laboratory Nucleic Acid Sequence Database (EMBL)(http://www.ebi.ac.uk/ebi__docs/embl__db.html) or versions thereof. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology, 12:76–80, 1994; Birren, et al., Genome Analysis, 1:543, 1997).

Any program designed for motif searching also has utility in the present invention. Sequence analysis programs designed for motif searching can be used for identification of cis elements. Preferred computer programs would include but are not limited to MEME, SIGNAL SCAN, and GENESCAN. Meme is a program that identifies conserved motifs (either nucleic acid or peptide) in a group of unaligned sequences. Meme saves these motifs as a set of profiles. These profiles can be used to search a database of sequences. A MEME algorithm (version 2.2) can be found in version 10.0 of the GCG package; MEME (T. Bailey and C. Elkan, Machine Learning, 21(1–2):51≧80,1995 and the location of the website is as follows: (http://www.sdsc.edu/MEME/meme/website/COPYRIGHT.html.). SignalScan is a program that identifies known motifs in the test sequences using information from other motif databases (Prestridge, D. S., CABIOS 7, 203–206 (1991). SignalScan version 4.0 information is available at the following website: http://biosci.cbs.umn.edu/software/sigscan.html. The ftp site for Signal Scan is ftp://biosci.cbs.umn.edu/software/sigscan.html. Databases used with Signal Scan include PLACE (http://www.dna.affrc.go.ip/htdocs/PLACE (Higo et al., Nucleic Acids Research 27(1):297–300 (1999) and TRANSFAC (Heinemeye, X. et al., Nucleic Acid Research 27(1):318–322) which can be found at the following website: http://transfac.gbf.de/. GeneScan is another suitable program for motif searching (Burge, C and Karlin, S. J. Mol. Biol. 268, 78–94 (1997) and version 1.0 information is available at the following website: http://gnomic.stanford.edu/GENESCANW.html. As used herein, "a target structural motif", or "target motif" refers any rationally selected sequence or combination of sequences in which the sequence(s) are chosen based on a three-dimensional configuration which is formed upon the folding of the target motif. There are a variety of target motifs known to those of skill in the art. Protein target motifs include but are not limited to, enzymatic active sites and signal sequences. Preferred target motifs of the present invention would include but are not limited to promoter sequences, cis elements, hairpin structures and other expression elements such as protein binding sequences.

As used herein, "search means" refers to one or more programs which are implemented on the computer-based system to compare a target sequence or target structural motif with the sequence information stored within the data storage means. Search means are used to identify fragments or regions of the sequences of the present invention that match a particular target sequence or target motif. Also, multiple sequences can be compared in order to identify common regions or motifs which may be responsible for specific functions. For example, cis elements or sequence domains which confer a specific expression profile can be identified when multiple promoter regions of similar classes of promoters are aligned and analyzed by certain software packages.

The present invention further provides systems, particularly computer-based systems, which contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. Those of skill in the art can appreciate that any number of available computer-based systems are suitable for use in the present invention and that such programs provide an efficient means for sequence data analysis compared with analysis by inspection of sequences without the aid of computer-based systems.

SEQ ID NOs: 6–35 are primers designed from the cDNA sequences identified from the computer-based sequence comparisons. These sequences are used to extend the nucleic acid sequence using polymerase chain reaction (PCR) amplification techniques (see for example, Mullis et al., Cold Spring Harbor Symp. Quant. Biol. 51:263, 1986; Erlich, et al., European Patent Appln. 50,424; European Patent Appln. 84,796, European Patent Appln. 258,017, European Patent Appln. 237,362; Mullis, European Patent Appln. 201,184; Mullis, et al., U.S. Pat. No. 4,683,202; Erlich, U.S. Pat. No. 4,582,788; and Saiki, et al., U.S. Pat. No. 4,683,194). A number of PCR amplification methods are known to those of skill in the art, and; are used to identify nucleic acid sequences adjacent to a known sequence. For example, inverse pcr (IP.CR) methods to amplify unknown DNA sequences adjacent to a core region of known sequence have been described. Other methods are also available such as capture PCR (Lagerstrom M., et al., PCR Methods Applic. 1:111, 1991, and walking PCR (Parker, JD et al., Nucleic Acids Res 19:3055, 1991). A number of manufacturers have also developed kits based on modifications of these methods for the purposes of identifying sequences of interest. Technical advances including improvements in primer and adaptor design, improvements in the polymerase enzyme, and thermocycler capabilities have facilitated quicker, efficient methods for isolating sequences of interest.

In a preferred embodiment, the flanking sequences containing the 5' regulatory elements of the present invention are isolated using a genome-walking approach (Universal GenomeWalker™ Kit, CLONTECH Laboratories, Inc., Palo, Alto, Calif.). In brief, the purified genomic DNA is subjected to a restriction enzyme digest which produces genomic DNA fragments with ends that are ligated with GenomeWalker™ adaptors. GenomeWalker™ primers are used along with gene specific primers in two consecutive PCR reactions (primary and nested PCR reactions) to produce PCR products containing the 5' regulatory sequences which are subsequently cloned and sequenced.

In addition to their use in modulating gene expression, the promoter sequences of the present invention also have utility as probes or primers in nucleic acid hybridization experiments.

The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, Nucl. Acids Res. 12:203–213, 1984; and Wetmur and Davidson, J. Mol. Biol. 31:349–370, 1968. Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 μg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results.

The nucleic acid sequences in SEQ ID NOs: 36–51 and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" is they can hybridize to one another with sufficient stability to permit them to remain annealed to one another under conventional "high stringency" conditions. Conventional stringency conditions are described by Sambrook, et al., Molecular Cloning, A Laboratory Manual, $2^{nd}$ Ed., Cold Spring Harbor Press, Cold Spring Harbor, New York, 1989, and by Haymes et al., Nucleic Acid Hybridization, A Practical Approach, IRL Press, Washington, D.C., 1985.

In a preferred embodiment, the nucleic acid sequences, SEQ ID NOs: 36–51 or a fragment, region, cis element, or oligomer of these sequences, may be used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation which can be supplied by commercial vendors.

Of course, fragments can also be obtained by other techniques such as by directly synthesizing the fragment by chemical means, as is commonly practiced by using an automated oligonucleotide synthesizer. Also, fragments can be obtained by application of nucleic acid reproduction technology, such as the PCR™ (polymerase chain reaction) technology by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment of a nucleic acid as used herein refers to any portion of the nucleic acid that is less than full-length. A fragment can also comprise at least a minimum length capable of hybridizing specifically with a native nucleic acid under stringent hybridization conditions as defined above. The length of such a minimal fragment is preferably at least 8 contiguous nucleotides, more preferably 15 contiguous nucleotides, even more preferably at least 20 contiguous nucleotides, and most preferably at least 30 contiguous nucleotides of a native nucleic acid sequence.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described, for example, in Molecular Cloning: A Laboratory Manual, 2nd ed., vol. 1–3, ed. Sambrook et al., Cold Spring Harbor Laboratory Press, Cold Spring Harbor, N.Y., 1989 (hereinafter, "Sambrook et al., 1989"); Current Protocols in Molecular Biology, ed.

Ausubel et al., Greene Publishing and Wiley-Interscience, New York, 1992 (with periodic updates) (hereinafter, "Ausubel et al., 1992); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequences of the promoters disclosed herein can be modified. Those skilled in the art can create DNA molecules that have variations in the nucleotide sequence. The nucleotide sequences of the present invention as shown in SEQ ID NOS: 36–51 may be modified or altered to enhance their control characteristics. One preferred method of alteration of a nucleic acid sequence is to use PCR to modify selected nucleotides or regions of sequences. These methods are known to those of skill in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NOS: 36–51 includes sequences of any length which are capable of regulating an operably linked DNA sequence. For example, the sequences as disclosed in SEQ ID NOS: 36–51 may be truncated or deleted and still retain be capable of regulating transcription of an operably linked DNA sequence. In a related embodiment, a cis element of the disclosed sequences may confer a particular specificity such as conferring enhanced expression of operably linked DNA sequences in embryogenic or callus tissues and therefore is also capable of regulating transcription. Consequently, any sequence fragments, portions, or regions of the disclosed sequences can be used as regulatory sequences, including, but not limited to cis elements or motifs. For example, one or more base pairs can be deleted from the 5' or 3' end of a promoter sequence to produce a "truncated" promoter. One or more base pairs can also be inserted, deleted, or substituted internally to a promoter sequence. Promoters can be constructed such that the promoter fragments or elements are operably linked, for example, by placing such a fragment upstream of a minimal promoter. A minimal or basal promoter is a piece of DNA which is capable of recruiting and binding the basal transcription machinery. One example of basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region which are capable of recruiting and binding transcription factors that modulate transcription, e.g., enhance, repress, render transcription hormone-dependent,; etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NOs: 36–51 or fragments, variants or derivatives thereof are incorporated into an expression vector cassette which includes the promoter regions of the present invention operably linked to a genetic component such as a selectable, screenable, or scorable marker gene. The disclosed nucleic acid sequences of the present invention are preferably operably linked to a genetic component such as a nucleic acid which confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility. The promoter sequences of the present invention can be used to regulate expression of any operably linked transcribable sequence. Particularly preferred operably linked transcribable sequences would include but are not limited to those sequences that are preferably expressed in embryogenic or callus tissue(s).

In a preferred embodiment, one genetic component produces a product which serves as a selection device and functions in a regenerable plant tissue to produce a compound which would confer upon the plant tissue resistance to an otherwise toxic compound. Genes of interest for use as a selectable, screenable, or scorable marker would include but are not limited to GUS (coding region for beta-glucuronidase, GFP (coding sequence for green fluorescent protein), LUX (coding region for luciferase), or antibiotic or herbicide tolerance genes. Examples of transposons and associated antibiotic resistance genes include the transposons Tns (bla), Tn5 (nptII), Tn7 (dhfr), penicillins, kanamycin (and neomycin, G418, bleomycin); methotrexate (and trimethoprim); chloramphenicol; kanamycin and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I–III, Laboratory Procedures and Their Applications Academic Press, New York, 1984. Particularly preferred selectable marker genes for use in the present invention would genes which confer resistance to compounds such as antibiotics like kanamycin, and herbicides like glyphosate (Della-Cioppa et al., Bio/Technology 5(6), 1987, U.S. Pat. No. 5,463,175, U.S. Pat. No. 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989). In a preferred embodiment, the host cell is a plant cell. A number of vectors suitable for stable transfection of plant cells or for the establishment of transgenic plants have been described in, e.g., Pouwels et al., Cloning Vectors: A Laboratory Manual, 1985, supp. 1987); Weissbach and Weissbach, Methods for Plant Molecular Biology, Academic Press, 1989; Gelvin et al., Plant Molecular Biology Manual, Kluwer Academic Publishers, 1990; and R. R. D. Croy, Plant Molecular Biology LabFax, BIOS Scientific Publishers, 1993. Plant expression vectors can include, for example, one or more cloned plant genes under the transcriptional control of 5' and 3' regulatory sequences. They can also include a selectable marker as described to select for host cells containing the construct. Such plant expression vectors also contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and a polyadenylation signal. Other types of regulatory sequence envisioned as genetic components in an expression vector include but is not limited to a non-translated leader sequence which can be coupled with the promoter. In a particularly preferred embodiment, the host cell is a plant cell and the plant expression vector comprises a promoter region as disclosed in SEQ ID NOs: 36–51. Plant expression vectors can also comprise additional sequences including but not limited to restriction enzyme sites which are useful for cloning purposes.

A number of promoters have utility for plant gene expression for any gene of interest including but not limited to selectable markers, scorable markers, genes for pest tolerance, disease tolerance, nutritional enhancements and any other gene of agronomic interest. Examples of constitutive promoters useful for plant gene expression include but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989) and the figwort mosaic virus (FMV) promoter (U.S. Pat. No. 5,378, 619 is a double border, right (RB) and left (LB) T-DNA borders, plant transformation vector consisting of the following genetic components: ZM-700267629 is the promoter for the *Zea mays* embryo enhanced expression isolated from a *Zea mays* embryo genomic library; I-Zm.Hsp70 intron is the intervening sequence of the maize heat shock protein as described in U.S. Pat. Nos. 5,593,874 and 5,859,347 herein incorporated by reference in their entirety); Ec.GUS:1 is the coding region for beta-glucuronidase from *E. coli*; T-AGRTU.nos is the termination signal from the nopaline synthase gene, P-CaMV.35S is the CaMV 35S promoter (U.S. Pat. No. 5,352,605 herein incorporated by reference in their entirety).

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or Safener. It may also be advantageous to employ (6) organ-specific promoters (e.g., Roshal et al., EMBO J. 6:1155, 1987; Schemthaner et al., EMBO J. 7:1249, 1988; Bustos et al., Plant Cell 1:839, 1989). The promoters of the present invention are embryonic cell enhanced and embryogenic tissue-enhanced or callus tissue enhanced plant promoters that can be operably linked to any gene of interest in an expression vector.

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region of plant genes (Thornburg et al., Proc. Natl. Acad. Sci. USA 84:744 (1987); An et al., Plant Cell 1:115 (1989), e.g., a 3' terminator region to increase mRNA stability of the mRNA, such as the PI-II terminator region of potato or the octopine or nopaline synthase 3' terminator regions. 5' non-translated regions of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362, 865 herein incorporated in its entirety). These additional upstream and downstream regulatory sequences may be derived from a source that is native or heterologous with respect to the other elements present on the expression vector.

The promoter sequences of the present invention are used to control gene expression in plant cells. More preferably the promoter sequences are used to control gene expression in plant seeds. Even more preferably the promoter sequences are used to control expression in plant embryos. The disclosed promoter sequences are genetic components which are part of vectors used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as B.t., pest tolerance, such as genes for fungal disease control, herbicide tolerance such as genes conferring glyphosate tolerance, and genes for quality improvements such as yield, nutritional enhancements such as vitamin, oil and amino acid composition, environmental or stress tolerances, or any desirable changes in plant physiology, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene which produces a protein or mRNA which expresses a phenotype or morpholgy change of interest are useful for the practice of the present invention.

In addition to regulatory elements or sequences located upstream (5') or within a DNA sequence, there are downstream (3') sequences which affect gene expression and thus the term regulatory sequence as used herein refers to any nucleotide sequence located upstream, within, or downstream to a DNA sequence which controls, mediates, or affects expression of a gene product in conjunction with the protein synthetic apparatus of the cell.

The promoter sequences of the present invention may be modified, for example for expression in other plant systems. In another approach, novel chimeric or hybrid promoters can be designed or engineered by a number of methods. Many promoters contain upstream sequences which activate, enhance or define the strength and/or specificity of the promoter (Atchison, Ann. Rev. Cell Biol. 4:127, 1988). T-DNA genes, for example contain "TATA" boxes defining the site of transcription initiation and other upstream elements located upstream of the transcription initiation site modulate transcription levels (Gelvin, In Transgenic Plants (Kung, S. -D. And Us, R., eds), San Diego: Academic Press, pp.49–87, 1988). Another chimeric promoter combined a trimer of the octopine synthase (ocs) activator to the mannopine synthase (mas) activator plus promoter and reported an increase in expression of a reporter gene (Min Ni et al., The Plant Journal 7:661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. No. 5,110,732 herein incorporated by reference in its entirety and U.S. Pat. No. 5,097,025 herein incorporated by reference in its entirety). Those of skill in the art are familiar with the standard resource materials which describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997); volume 2, Detecting Genes, (1998); volume 3, Cloning Systems, (1999), volume 4, Mapping Genomes, (1999), Cold Spring Harbor, N.Y.).

The promoter sequences of the present invention can be incorporated into an expression vector using screenable or scorable markers as described and tested in transient analyses which provide an indication of gene expression in stable plant systems. Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612. 1993), electroporation of leaf protoplasts of wheat (Sethi et al., J. Crop Sci. 52: 152, 1983; electroporation of protoplast prepared from corn tissue (Sheen, J. The Plant Cell 3: 225, 1991, or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include but are not limited to leaf base tissues, callus, cotyledons, roots, endosperm, embryogenic tissue, floral tissue, pollen, and epidermal tissue.

Any scorable or screenable marker can be used in a transient assay. Preferred marker genes for transient analyses of the promoters or 5' regulatory sequences of the present invention include a GUS gene (coding sequence for β-glucuronidase) or a GFP gene (coding sequence for green fluorescent protein). The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the promoter sequences when operatively linked to genes of agronomic interest in stable plants. Ultimately, the 5' regulatory sequences of the present invention are directly incorporated into suitable plant transformation expression vectors with the 5' regulatory sequences operatively linked to selectable markers and genes of interest, transformed into plants and the stably transformed plants and progeny thereof analyzed for the desired expression profile conferred by the 5' regulatory sequences. Those of skill in the art are aware of the vectors and suitable for plant transformation. Suitable vectors would include but are not limited to disarmed Ti-plasmids for Agrobacterium-mediated methods. These vectors can contain a resistance marker, 1-2 T-DNA borders, and origins of replication for *E. coli* and Agrobacterium along with one or more genes of interest and associated regulatory regions. Those of skill in the art are aware that for Agrobacterium-mediated approaches a number of strains and methods are available. Such strains would include but are not limited to Agrobacterium strains C58, LBA4404, EHA101 and EHA105. Particularly preferred strains are *Agrobacterium tumefaciens* strains. Other DNA delivery systems for plant transformation are also known to those of skill in the art and include but is not limited to particle bombardment of selected plant tissues. Other DNA delivery systems for plant transformation are also known to those of skill in the art and include but is not limited to particle bombardment of selected plant tissues generally optimized for the particular plant host of interest.

Exemplary nucleic acids which may be introduced by the methods encompassed by the present invention include, for example, DNA sequences or genes from another species, or even genes or sequences which originate with or are present in the same species, but are incorporated into recipient cells by genetic engineering methods rather than classical reproduction or breeding techniques. However, the term exogenous, is also intended to refer to genes which are not normally present in the cell being transformed, or perhaps simply not present in the form, structure, etc., as found in the transforming DNA segment or gene, or genes which are normally present yet which one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. No. 5,004,863; U.S. Pat. No. 5,159,135; U.S. Pat. No. 5,518,908, WO 97/43430), soybean (U.S. Pat. No. 5,569,834; U.S. Pat. No. 5,416,011; McCabe et al., Bio/Technology, 6:923, 1988; Christou et al., Plant Physiol., 87:671, 1988); Brassica (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes, C. A., et al., Science, 240: 204, 1988; Gordon-Kamm, et al., Plant Cell, 2: 603, 1990; Fromm, et al., Bio/Technology, 8: 833, 1990; Koziel, et al., Bio/Technology, 11: 194, 1993); oats (*Avena sativa*; Somers, et al., Bio/Technology, 10: 1589, 1992); orchardgrass (*Dactylis glomerata*; Horn, et al., Plant Cell Rep., 7: 469, 1988); rice (*Oryza sativa*, including indica and japonica varieties, Toriyama, et al., Bio/Technology, 6: 10, 1988; Zhang, et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou, et al., Bio/Technology, 9: 957, 1991); sorghum (*Sorghum bicolor*; Casas, A. M., et al., Proc. Natl. Acad. Sci. U.S.A., 90: 11212, 1993); sugar cane (Saccharum spp.; Bower and Birch, Plant J., 2: 409, 1992); tall fescue (*Festuca arundinacea*; Wang, Z. Y. et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks T., et al., Plant Physiol., 102: 1077, 1993; Becker, et al., Plant, J. 5: 299, 1994), and alfalfa (Masoud, S. A., et al., Transgen. Res., 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings is to be interpreted as illustrative and not in a limiting sense.

EXAMPLES

A number of tissues and plant developmental stages are selected for preparation of the corn libraries. Those of skill in the art are aware of the variations in tissue selection and preparation that occur from one tissue sampler to the next. The following are the conditions for the target libraries.

Example 1

Embryo tissue from corn thirteen days after pollination (13-DAP) (SATMON033 library) or twenty-one days after pollination (21-DAP) (SATMON017 library) is used as the source material for the Embryo-13-DAP or Embryo-21-DAP cDNA libraries, respectively. The libraries are generated from corn (DK604, Dekalb Genetics, Dekalb, Ill. U.S.A.). Seeds are planted at a depth of about 3 cm in soil into 2"–3" pots containing Metro 200 growing medium and transplanted into larger 10" pots containing the same soil after 2–3 weeks. Peters 15-16-17 fertilizer is applied abut 3 times per week after transplanting, at a strength of 150 ppm N. 2–3 times during the life of the plant from transplanting to flowering. A total of about 900 mg Fe is added to each pot which is added two to three times during the lifetime of the plant, from transplanting to flowering. Corn plants are grown in the greenhouse in 15 hr day/9 hr night cycles. The daytime temperature is approximately 80° F and the night temperature is approximately 70° F. Supplemental lighting is provided by 1000 W sodium vapor lamps.

Corn plants selected are beyond the V10 stage and ear shoots ready for fertilization are enclosed in a paper bag before silk emergence to withhold the pollen. Thirteen days after pollination (13-DAP) or twenty-one days after pollination (21-DAP), the ears are pulled out and the kernels picked out of the ears. Each kernel is dissected into the embryo and endosperm and the aleurone layer is removed. After dissection, the embryos are frozen in liquid nitrogen and stored at −80° C. until RNA preparation.

For preparation of the the regenerating HI II type II callus library (SATMON025), petri plates containing callus initiation media is prepared. The medium contains N6 salts and vitamins, 3% sucrose, 2.3 g/liter proline, 0.1 g/liter casein hydrolysate, 2 mg/liter 2,4-D, 15.3 mg/liter AgNO3 and 0.8% Bacto-Agar and the media is adjusted to pH 6.0 before autoclaving. At 9–11 days after pollination, an ear with immature embryos measuring approximately 1–2 mm in length is selected. The husks and silks are removed and the ear broken into halves and placed in an autoclaved solution of Clorox/tween 20. The ear is rinsed with deionized water and each embryo is extracted from the kernel. Intact embryos are placed in contact with the medium, scutellum side up. Multiple embryos are plated on each plate and the plates are incubated in the dark at 25° C. (all media ingredients are commercially available and most are purchased from Sigma Chemical Co., St. Louis, Mo.). Friable type II callus tissue formed is transferred to the media described without AgNO3 and subcultured every 7–10 days. About 4 weeks after embryo isolation, the callus is scooped out of the plates and frozen in liquid nitrogen. The harvested tissue is stored at −80° C. until RNA preparation.

The RNA is purified from the harvested tissue using Trizol reagent available from Life Technologies (Gaithersburg, Md.) essentially as recommended by the manufacturer. Poly A+ RNA (mRNA) is purified using magnetic oligo dT beads essentially as recommended by the manufacturer (Dynabeads, Dynal Corporation, Lake Success, N.Y.).

Construction of cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md.) is used, following the conditions suggested by the manufacturer.

The cDNA libraries are plated on LB agar containing the appropriate antibiotics for selection and incubated at 37° C. for a sufficient time to allow the growth of individual colonies. Single colonies are individually placed in each well of a 96-well microtiter plate containing LB liquid including selective antibiotics. The plates are incubated overnight at approximately 37° C. with gentle shaking to promote growth of the cultures. The plasmid DNA is isolated from each clone using Qiaprep Plasmid Isolation kits, using the conditions recommended by the manufacturer (Qiagen Inc., Santa Clara, Calif.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif.

Example 2

The promoters are identified from a database of EST sequences derived from the cDNA libraries prepared from various corn tissues including embryonic cells and embryogenic tissue-enhanced or callus tissue-enhanced mRNAs. The sequences are also used as query sequences against GenBank databases which contain previously identified and annotated sequences and searched for regions of homology using BLAST programs. The selection of expressed sequence tags (ESTs) for subsequent promoter isolation is reflective of the presence of one or more sequences among the representative ESTs from a random sampling of an individual cDNA library or collection of cDNA libraries. To identify regulatory sequences that regulate the expression of transcripts in the maize embryo, a subsetting function is performed, requesting all ESTs found in target embryo libraries and absent or in lower abundance in other non-target EST libraries in the database. The resulting candidate ESTs are subjected to an electronic northern function in which the putative tissue expression profile and abundance levels in a library for a given EST is displayed. Target ESTs with the desired tissue expression profile and abundance are identified and gene specific primers are designed based on the identified EST sequences.

Product score refers to the strength of a BLAST match between a EST clone of interest and a GenBank sequence. Percent abundance relates to the number of times the members of a group of related expressed sequences appears in a library the EST is derived from. Any number of queries can be executed to obtain the desired ESTs and will depend upon the EST database and computer programs available for sequence analyses. For the present invention, sequences are identified by selection of desired values for relative abundance, stringency, and/or product score. For the promoter sequences of SEQ ID NOs: 36–51, a target abundance of $\geq 1$ is selected with a background of $\leq 0$, a stringency of $\geq 50$ and product score of of $\leq 100$.

The clone IDs for EST sequences of interest representing cDNAs with the targeted expression profile are identified based on the these database queries. Table 1 provides background clone ID (EST) information, library sources, and GenBank identifier (gi) information for the ESTs used for subsequent isolation of the promoter sequences of SEQ ID NOS: 36–51. Sequence annotation is listed for clone IDs based on a GenBank BLAST search with a p-value cut-off of $10^{-8}$. The information is subject to change as new sequences are submitted to the sequence databases. The annotations for the ESTs are listed as follows with the annotation information in parentheses: Clone 700614347 (*Oryza sativa* subsp. Indica embryo-specific protein (Ose731) gene, complete cds).; Clone 700257959 (*Oryza sativa* globulin-like protein mRNA, clone Ose709, partial cds).; Clone 700265029 (*Zea mays* myo-inositol 1-phosphate synthase mRNA, complete cds).; Clone 700321659 (*Zea mays* mRNA for group 3 Lea protein MGL3).; Clone 700616085 (*Oryza sativa* subsp. Indica embryo-specific protein (Ose731) gene, complete cds).

TABLE 1

Promoter Summary Information

| SEQ ID No. | Clone ID | Library Source | GenBank Identifier (gi) |
|---|---|---|---|
| 36 | 700264271 | embryo, 21-DAP | none |
| 37 | 700265872 | embryo, 21-DAP | none |
| 38 | 700263624 | embryo, 21-DAP | none |
| 39 | 700267629 | embryo, 21-DAP | none |
| 40 | 700258061 | embryo, 21-DAP | none |
| 41 | 700614347 | embryo, 13-DAP | g4105691 |
| 42 | 700257959 | embryo, 21-DAP | g4097099 |
| 43 | 700265029 | embryo, 21-DAP | g3108052 |
| 44 | 700266438 | embryo, 21-DAP | none |
| 45 | 700259522 | embryo, 21-DAP | none |
| 46 | 700321659 | corn callus | g444044 |
| 51 | 700266176 | embryo, 21-DAP | none |
| 47 | 700257969 | embryo, 21-DAP | none |
| 48. | 700613864 | embryo, 13-DAP | none |
| 49, 50 | 700260279 | embryo, 21-DAP | none |

Example 3

The genomic libraries are prepared from corn DNA (from maize hybrid Fr27xFrMo17) isolated using a CsCl purification protocol according to Ausubel et al., 1992, or by a CTAB purification method (Rogers and Bendich, Plant Mol. Biol., 5:69 (1985). Reagents are available commercially (for example, Sigma Chemical Co., St. Louis, Mo.). The libraries are prepared according to manufacturer instructions (GENOME WALKER, is a trademark of CLONTECH laboratories, Inc, Palo Alto, Calif.). In separate reactions, genomic DNA is subjected to restriction enzyme digestion overnight at 37° C. with the following blunt-end endonucleases: EcoRV, ScaI, DraI, PvuII, or StuI (CLONTECH Laboratories, Inc. Palo Alto, Calif.). The reaction mixtures are extracted with phenol:chloroform, ethanol precipitated, and resuspended in Tris-EDTA buffer. The purified blunt-ended genomic DNA fragments are then ligated to the GenomeWalker™ adaptors and ligation of the resulting DNA fragments to adaptors were done according to manufacturer protocol. The GenomeWalker™ sub-libraries are aliquoted and stored at −20° C.

Genomic DNA ligated to the GenomeWalker™ adaptor (above) is subjected to a primary round of PCR amplification with gene-specific primer 1 (GSP1) and a primer which anneals to the Adaptor sequence, adaptor primer 1 (AP1) shown in SEQ ID NO: 1. A diluted (1:50) aliquot of the primary PCR reaction is used as the input DNA for a nested round of PCR amplification with gene-specific primer 2 (GSP2) and adaptor primer 2 (AP2) shown in SEQ ID NO: 2, or adaptor primer 3. (AP3) shown in SEQ ID NO: 3. The annealing temperatures of the Genome Walker primary primer (AP1) and nested primer (AP2) are 59° C. and 71° C., respectively. Generally, gene specific primers are designed to have the following characteristics: 26–30 nucleotides in length, GC content of 40–60% with resulting temperatures for most of the gene specific primers in the high 60° C. range or about 70° C. The Taq polymerase used is Amplitaq Gold™, available through Perkin-Elmer Biosystems (Branchbury, N.J.). A number of temperature cycling instruments and reagent kits are commercially available from a number of manufacturers for performing PCR experiments and include those available from PE Biosystems (Foster City, Calif.), Strategene (La Jolla, Calif.), and MJ Research Inc. (Watertown, Mass.). Following a primary PCR reaction, an aliquot is taken (10–15 µl) for agarose gel analysis. Each unknown is amplified from 5 sub-genomic libraries and a negative control (without DNA).

The PCR components and conditions are outlined below:

PRIMARY PCR

| Component | Amount/Volume required |
|---|---|
| Sub-library aliquot | 1 µl |
| Gene-specific primer 1 | 1 µl (100 pmol) |
| GenomeWalker ™ Adaptor primer 1 (AP1) | 1 µl |
| dNTP mix (10 mM of each dNTP) | 1 µl |
| DMSO | 2.5 µl (or 2–5% final concentration) |
| 10X PCR buffer (containing MgCl$_2$) | 5 µl (final concentration of 1X) |
| Amplitaq Gold ™ | 0.5 µl |
| Distilled Water | For final reaction volume of 50 µl |

Reaction Conditions for Primary PCR:

A. 9 minutes at 95° C.
B. 94° C. for 2 seconds, 70° C. for 3 minutes; repeat 94° C./70° C. cycling for total of 7 times
C. 94° C. for 2 seconds, 65° C. for 3 minutes; repeat 94° C./65° C. cycling for total of 36 times
D. 65° C. for 4 minutes as a final extension
E. 10° C. for an extended incubation

NESTED PCR (secondary PCR reaction)

| Component | Amount/Volume Required |
|---|---|
| 1:50 dilution of the primary PCR reaction | 1 µl |
| Gene-specific primer 2 | 1 µl (100 pmol) |
| GenomeWalker ™ Adaptor primer 2 or 3 (AP2 or AP3)) | 1 µl |
| dNTP mix (10 mM of each dNTP) | 1 µl |
| DMSO | 2.5 µl |
| 10X PCR buffer (containing MgCl$_2$) | 5 µl (final concentration of 1X) |
| Amplitaq Gold ™ | 0.5 µl |
| Distilled water | to final reaction volume of 50 µl |

Reaction Conditions for Nested PCR:

A. 9 minutes at 95° C.
B. 94° C. for 2 seconds, 70° C. for 3 minutes; repeat 94° C./70° C. cycling for total of 5 times
C. 94° C. for 2 seconds, 65° C. for 3 minutes; repeat 94° C./65° C. cycling for total of 24 times
D. 65° C. for 4 minutes as a final extension
E. 10° C. for an extended incubation For the isolation of the promoter sequence SEQ ID NO:36 (clone ID 700264271), SEQ ID NO:1 (A) is combined with SEQ ID NO:6 in the primary PCR reaction. For the nested PCR reaction SEQ ID NO:2 is combined with SEQ ID NO:7 in a secondary PCR reaction.

For the isolation of the promoter sequence SEQ ID NO:37 (clone ID 700265872), SEQ ID NO:1 is combined with SEQ ID No. 8 in the primary PCR reaction. For the nested PCR reaction, SEQ ID NO:2 is combined with SEQ ID NO:9 in a secondary PCR reaction.

For the isolation of the promoter sequence SEQ ID NO:38 (clone ID 700263624), SEQ ID NO:1 is combined with SEQ ID NO:10 in the primary PCR reaction. For the nested PCR reaction SEQ ID NO:2 is combined with SEQ ID NO:11 in a secondary PCR reaction.

For the isolation of the promoter sequence SEQ ID NO:39 (clone ID 700267629), SEQ ID NO:1 is combined with SEQ ID NO:12 in the primary PCR reaction. For the nested PCR react ion SEQ ID NO:1 is combined with SEQ ID NO:13 in a secondary PCR reaction.

For the isolation of the promoter sequence SEQ ID NO:40 (clone ID 700258061), SEQ ID NO:1 is combined with SEQ ID NO:14 in the primary PCR reaction. For the nested PCR reaction SEQ ID NO:2 is combined with SEQ ID NO:15 in a secondary PCR reaction.

For the isolation of the promoter sequence SEQ ID NO: 41 (clone ID 700614347), SEQ ID NO:1 is combined with SEQ ID NO:16 in the primary PCR reaction. For the nested PCR reaction, SEQ ID NO:2 is combined with SEQ ID NO:17 in a secondary PCR reaction.

For the isolation of the promoter sequence SEQ ID NO:42 (clone ID 700257959), SEQ ID NO:1 is combined with SEQ ID NO:18 in the primary PCR reaction. For the nested PCR reaction SEQ ID NO:2 is combined with SEQ ID NO:19 in a secondary PCR reaction.

For the isolation of the promoter sequence SEQ ID NO:43 (clone ID 700265029), SEQ ID NO:1 is combined with SEQ ID NO:20 in the primary PCR reaction. For the nested PCR reaction SEQ ID NO:2 is combined with SEQ ID NO:21 in a secondary PCR reaction.

For the isolation of promoter sequence SEQ ID NO:44 (clone ID 700266438), SEQ ID NO:1 is combined with SEQ ID NO:22 in a primary PCR reaction. For the nested PCR reaction SEQ ID NO:2 is combined with SEQ ID NO:23 in a secondary PCR reaction.

For the isolation of promoter sequence SEQ ID NO:45 (clone ID 700259522), SEQ ID NO:1 is combined with SEQ ID NO:24 in the primary PCR reaction. For the nested PCR reaction SEQ ID NO:2 is combined with SEQ ID NO:25 in a secondary PCR reaction.

For the isolation of promoter sequence SEQ ID NO:46 (clone ID 700321659), SEQ ID NO:1 is combined with SEQ ID NO:26 in the primary PCR reaction. For the nested PCR reaction SEQ ID NO:2 is combined with SEQ ID NO:27 in a secondary PCR reaction.

For the isolation of promoter sequence SEQ ID NO:47 (clone ID 700257969), SEQ ID NO:1 is combined with SEQ ID NO:28 in the primary PCR reaction. For the nested PCR reaction SEQ ID NO:2 is combined with SEQ ID NO:29 in a secondary PCR reaction.

For the isolation of promoter sequence SEQ ID NO:48 (clone ID 700613864), SEQ ID NO:1 is combined with SEQ ID NO:30 in the primary PCR reaction. For the nested PCR reaction SEQ ID NO:2 is combined with SEQ ID NO:31 in a secondary PCR reaction.

For the isolation of promoter sequence SEQ ID NO:49 (clone ID 700260279-PvuII library), SEQ ID NO:1 is combined with SEQ ID NO:32 in the primary PCR reaction. For the nested PCR reaction SEQ ID NO:3 is combined with SEQ ID NO:33 in a secondary PCR reaction.

For the isolation of promoter sequence SEQ ID NO:50 (clone ID 700260279-DraI library), SEQ ID NO:1 is combined with SEQ ID NO:32 in the primary PCR reaction. For the nested PCR reaction SEQ ID NO:3 is combined with SEQ ID NO:34 in a secondary PCR reaction.

For the isolation of promoter sequence SEQ ID NO:51 (clone ID 700266176), SEQ ID NO:1 is combined with SEQ ID NO:34 in the primary PCR reaction. For the nested PCR reaction SEQ ID NO:3 is combined with SEQ ID NO:35 in a secondary PCR reaction.

Example 4

The DNA fragments resulting from the nested PCR amplification are isolated and gel purified. A 40 μl aliquot of the secondary PCR is electrophoresed in an agarose gel. The DNA fragment of the secondary PCR product is purified from the agarose gel using the BIO101 Geneclean II Kit (Midwest Scientific, Valley Park, Mo.) following the conditions suggested by the manufacturer. The purified DNA is ligated to pGEM-T Easy vector (pGEM-T Easy Vector System I, Promega Corp., Madison, Wis.) following the conditions recommended by the manufacturer. An aliquot of the ligation reaction is transformed into a suitable *E. coli* host such as DH10B and the cells plated on selection medium (for DH10B, 100 μg/ml carbenicillin). Bacterial transformants are selected, grown in liquid culture, and the plasmid DNA isolated using a commercially available kit such as the Qiaprep Spin Microprep Kit (Qiagen Corp., Valencia, Calif.). Purified plasmid containing the predicted insert size based on restriction enzyme analysis are sequenced using the dye terminator method in both directions using the M13 forward and reverse primers which are shown in SEQ ID NO:4 (M13 forward primer) and S (M13 reverse primer). Restriction enzymes used are also commercially available from a number of manufacturers (for example, Boehringer Mannheim (Indianapolis, Ind.). The 5' flanking region containing the promoter sequence is determined and shown in SEQ ID NOS: 36–51. Engineering restriction sites for cloning the promoter fragments into suitable vectors is typically done using PCR methods known to those of skill in the art.

Example 5

For transient expression analyses, promoter fragments are cloned into expression vectors. If an start codon (AUG) of a target promoter gene is identified, the promoter fragment is cloned into a vector such as shown in FIG. 1 (pMON19469) in place of the P-CaMV.35S genetic element. If an AUG is not identified, the promoter fragment is cloned into an expression vector modified to enable translational fusions with a reporter gene such as GUS or GFP.

The expression constructs are tested in a transient plant assay. A number of assays are available and known to those of skill in the art. For a histochemical assay for GUS activity, embryos are collected 13-DAP and placed on a culture media such as MS media (Physiologia Plantarum 15:473 (1962), along with Type II embryogenic callus. To analyze the promoters in a transient assay, slices of endosperm from 13-DAP kernels and segments of etiolated leaf from seedlings 14 days after germination (DAG) are bombarded with the expression vector DNA using a suitable particle gun apparatus (see for example Christou et al., Plant Physiol., 87:671 (1989); Klein et al., Proc. Natl. Acad. Sci. USA, 85:4305 (1988); Ye, G. -N., et al., Plant Mol. Biol., 15:809 (1990). Each expression vector is bombarded onto two independent plates. The tissues are allowed to recover for 48 hours and then stained with X-Gluc (5-bromo-4-chloro-3-indoyl β-D-glucuronide) to detect expression of the GUS gene in the tissues of interest (Jefferson et al., EMBO J., 6:3901 (1987).

Example 6

Figure 2:
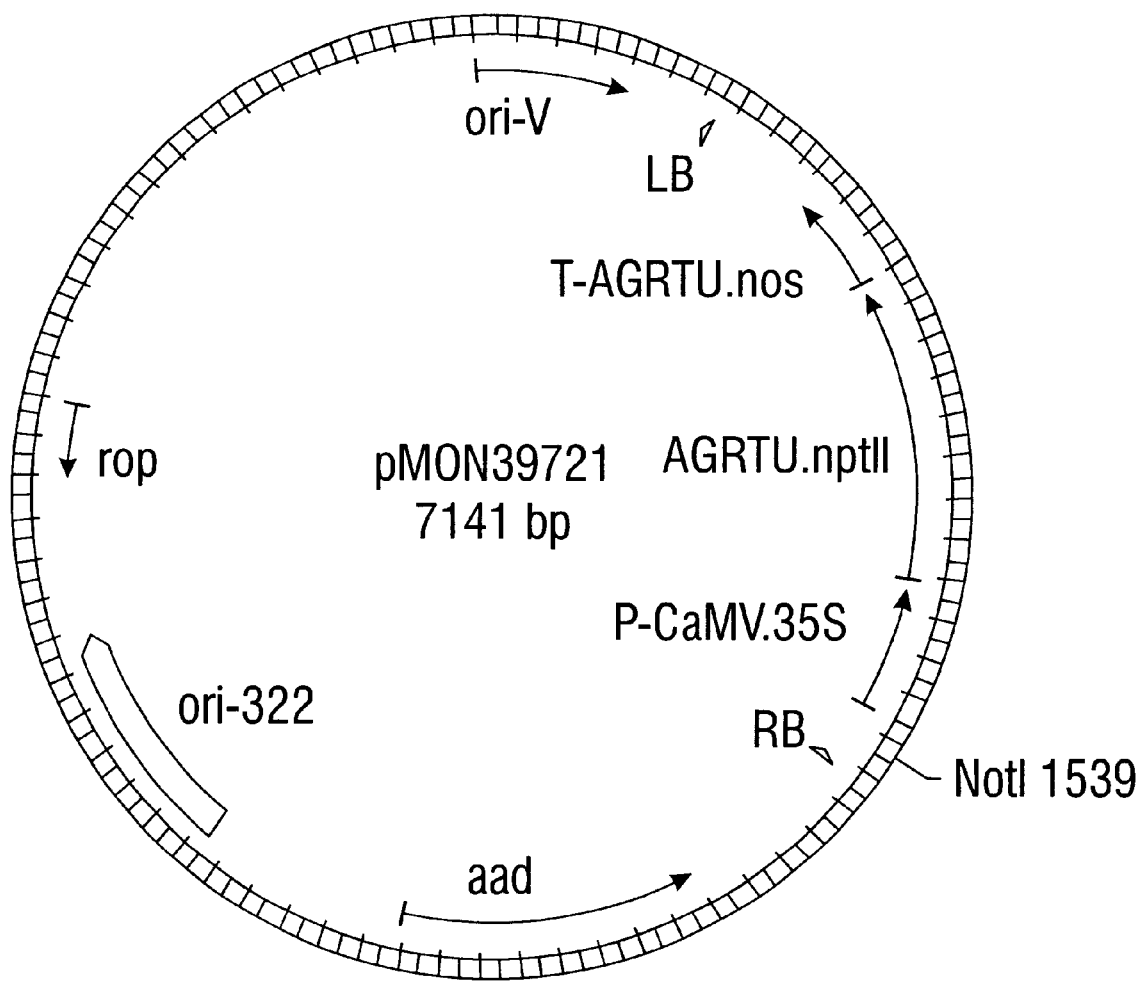
FIG. 2 is a plasmid map of pMON39721

For stable plant transformation the promoter sequences are cloned into a plant transformation vector such as shown in FIG. 2 (pMON39721) and transformed into a target crop of interest via an appropriate delivery system such as Agrobacterium-mediated transformation (see for example U.S. Pat. Nos. 5,569,834, 5,416,011, 5,631,152, 5,159,135 and 5,004,863 all of which are herein incorporated by reference in their entirety) or particle bombardment methods (see for example Patent Applns. WO 92/15675, WO 97/48814 and European Patent Appln. 586,355, and U.S. Pat. Nos. 5,120,657, 5,503,998, 5,830,728 and 5,015,580, all of which are herein incorporated by reference in their entirety).

Figure 3:
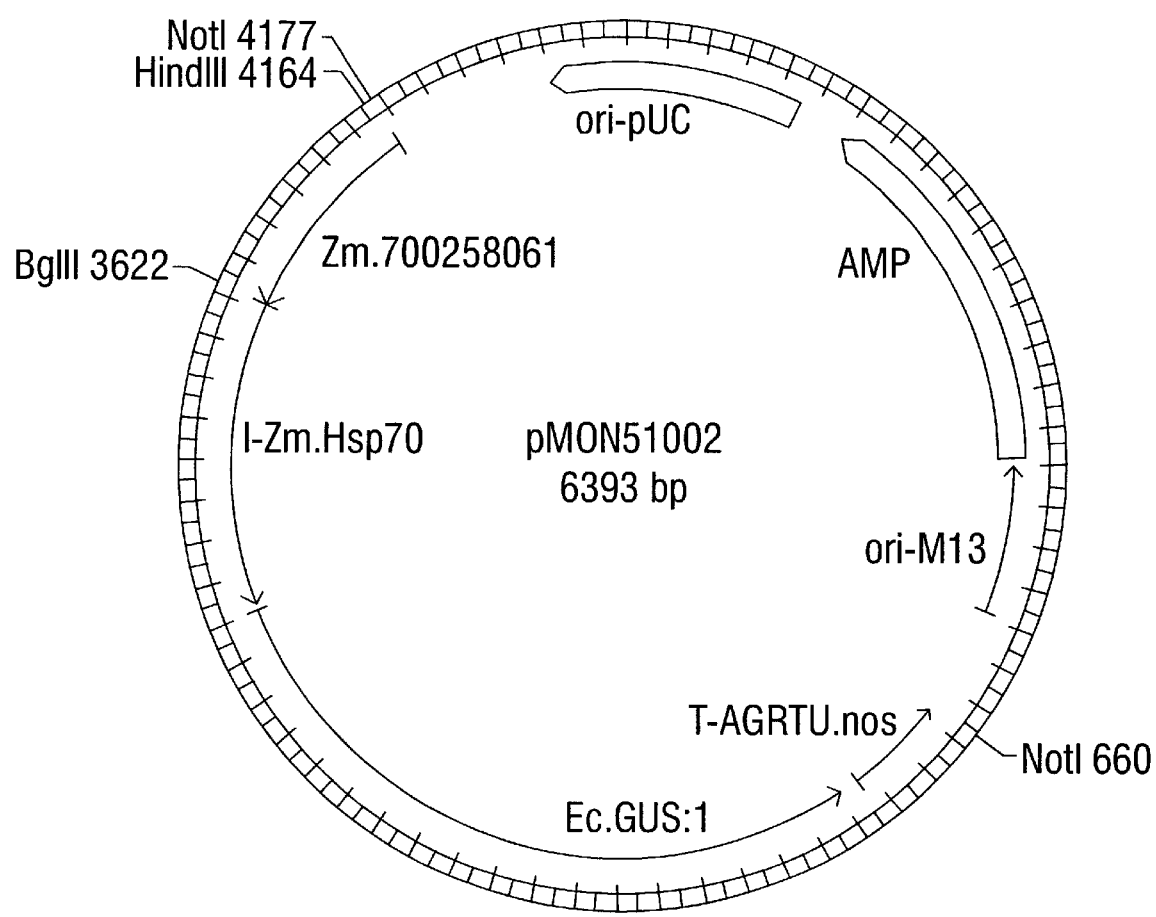
FIG. 3 is a plasmid map of pMON51002
Figure 4:
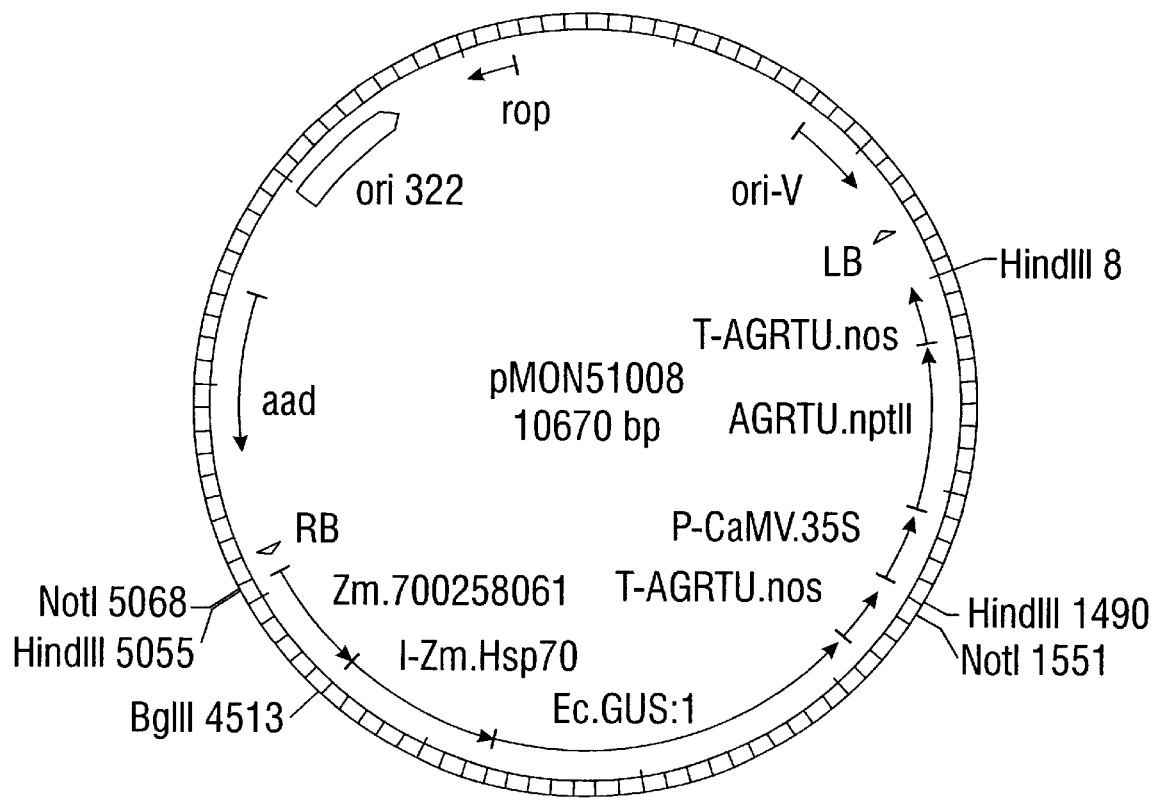
FIG. 4 is a plasmid map of pMON51008
Figure 5:
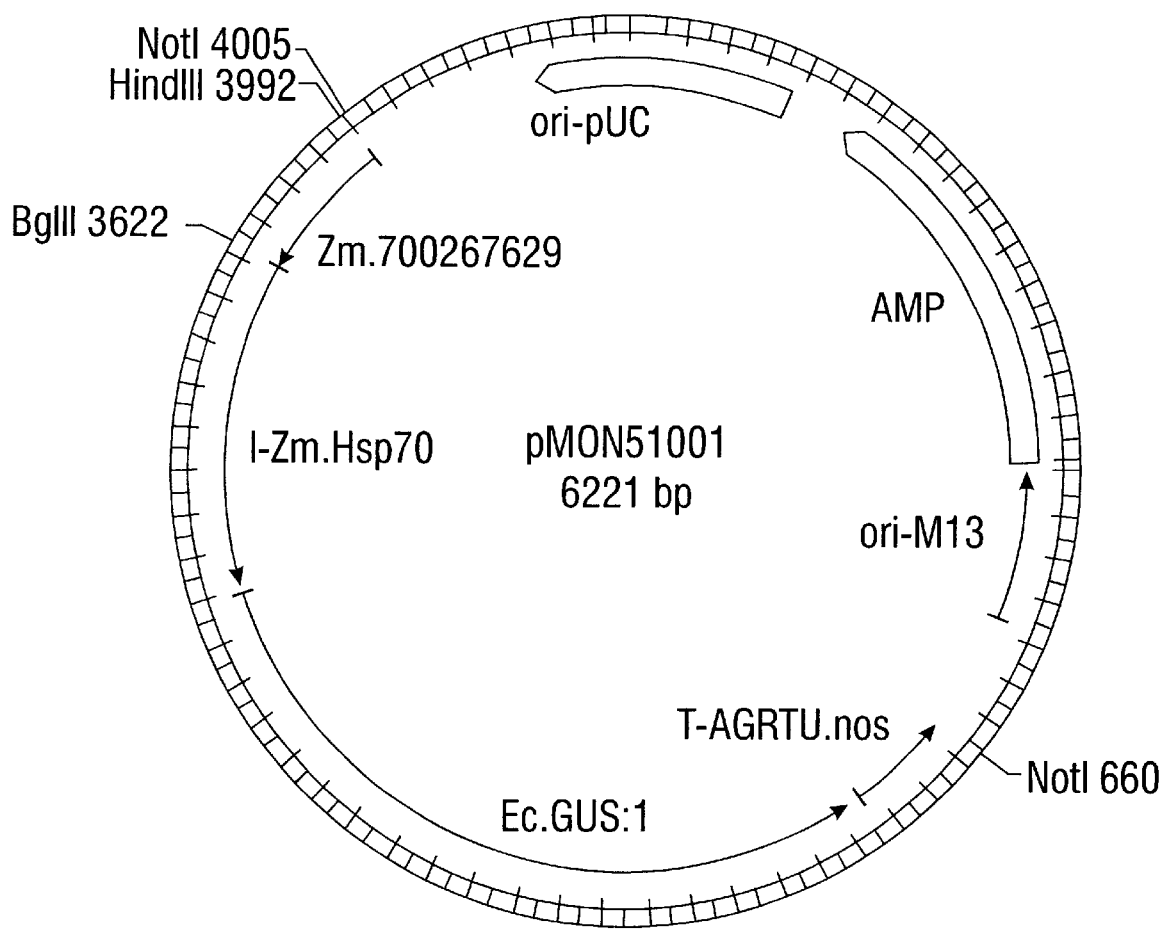
FIG. 5 is a plasmid map of pMON51001
Figure 6:
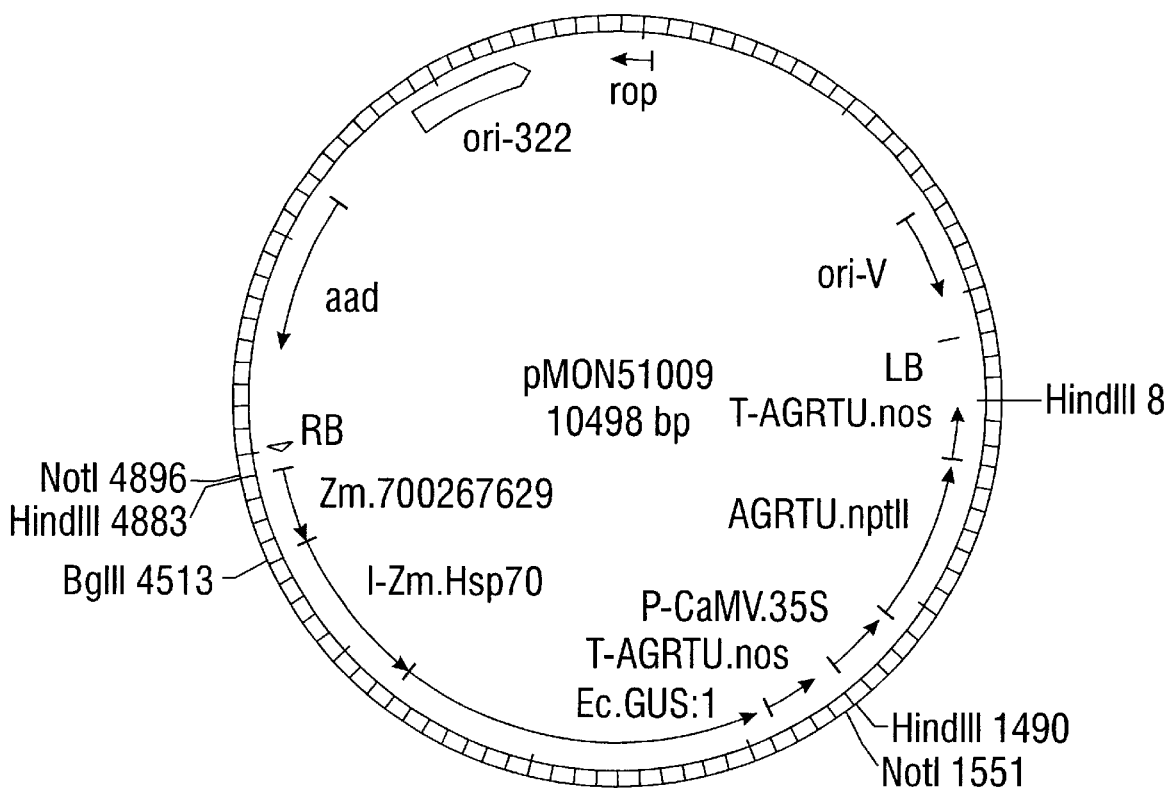
FIG. 6 is a plasmid map of pMON51009
Figure 7:
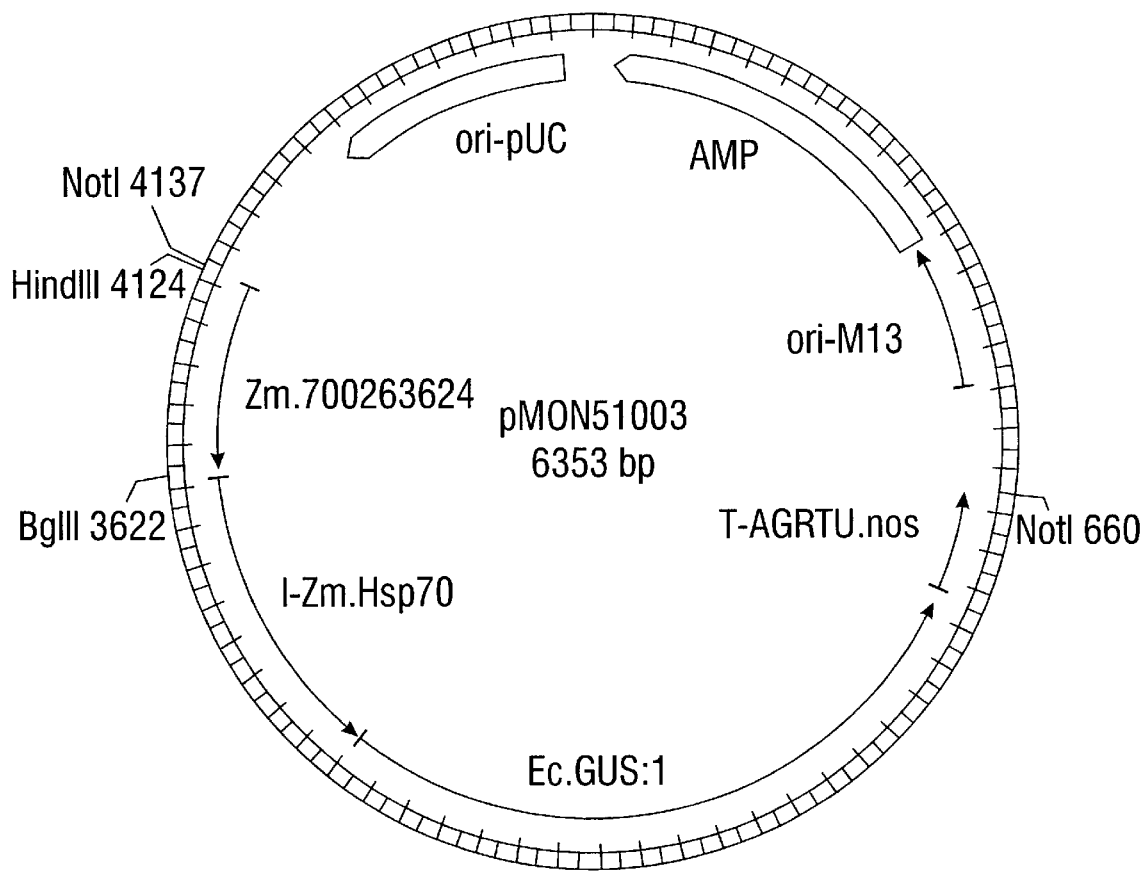
FIG. 7 is a plasmid map of pMON51003
Figure 8:
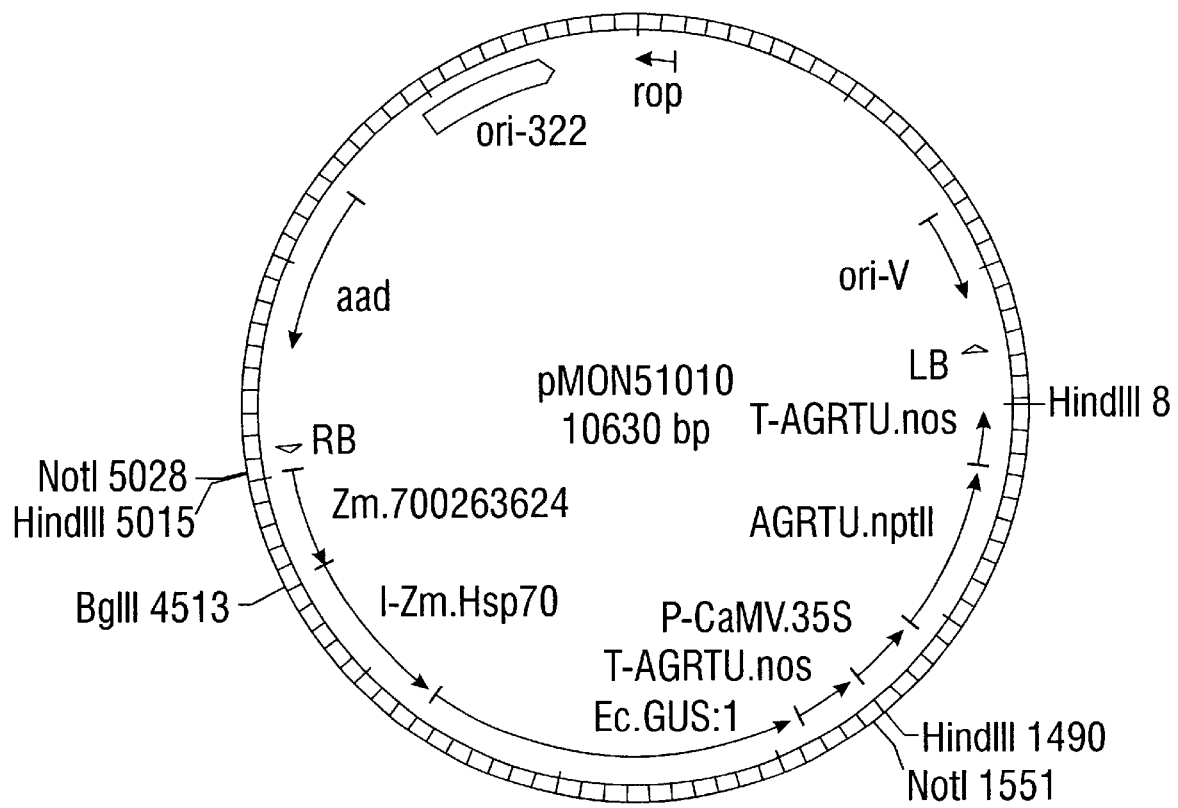
FIG. 8 is a plasmid map of pMON51010

The NotI fragment from pMON51002 (FIG. 3.) including promoter Zm.700258061(SEQ ID NO:40) driving expression of the Ec.GUS gene was isolated and cloned into NotI site of the plant transformation vector pMON39721 (FIG. 2) to generate pMON51008 (FIG. 4) for stable transformation of corn. The NotI fragment from pMON51001 (FIG. 5) including promoter Zm.700267629 (SEQ ID NO:39) driving expression of the Ec.GUS gene was isolated and cloned into NotI site of the plant transformation vector pMON39721 to generate pMON51009 (FIG. 9) for stable transformation of corn. The NotI fragment from pMON51003 (FIG. 7) including promoter Zm.700263624 (SEQ ID NO:38) driving expression of the Ec.GUS gene was isolated and cloned into NotI site of plant transformation vector pMON39721 to generate pMON51010 (FIG. 8) for stable transformation of corn. Methods well known in the art of molecular biology such as endonuclease digestion, DNA fragment purification, ligation, bacteria transformation, antibiotic selection, plasmid purification were used in the construction of these plant transformation constructs (Sambrook et al., 1989). The plant transformation constructs were transfered into *Agrobacterium tumefaciens* by a triparental mating procedure (Ditta et al. Proc. Natl Acad. Sci USA 77:7347 (1980).

*Agrobacterium tumefaciens* (ABI strain) was employed and cultured in LB liquid medium (50 ml medium per 250 ml flask) containing 100 mg/L kanamycin, 50 mg/L spectinomycin and 25 mg/L chloramphenicol (Sigma-Aldrich, St. Louis, Mo.) for about 24 hours (on a rotary shacker at 150–160 rpm) at 27° C. The culture was spun down at 3400 rpm and re-suspended into AB liquid medium (the OD was adjusted to 0.2 at 660 nm) containing 12 the level of spectinomycin and kanamycin used for LB, in addition of 200 μM of acetosyringone (AS; used for the induction of virulence) in a 250 ml flask. After cultured for 15–16 hours in the same condition as LB culture, the agrobacterium suspension was harvested and washed in ½ MS VI medium containing AS and centrifuged again before resuspending in the ½ MS PL medium (also contain the same level of AS). The final concentration of Agrobacterium was about 1×109 cfu/ml (which is equal to an OD of 1.0 at 660).

A maize triple hybrid of (Pa91×H99)×A188 were employed for transformation in our experiments. Maize immature embryos with a size of 0.5 mm to 2.0 mm long were aseptically collected and immersed into ½ MS PL liquid medium containing Agrobacterium and 200 μM of AS for 30 minutes. The immature embryos were dried on a piece of paper before plated onto ½ MS co-culture medium containing 3.0 mg/L 2,4-D, 200 μM acetosyringone, 2% sucrose, 1% glucose, 12 mM of proline and 20 μM silver nitrate and cultured at 23° C. for 2 or 3 days. Embryos were then transferred to a 15AA delay medium consisting of 15AA macro and micro salts, 1 mg/L 2,4-D, 12 mM proline and 500 mg/l carbenicillin and cultured at 27° C. for 5 days. The embryos were transferred to the first selection medium containing 15AA medium containing 1.0 mg/L 2,4-D, 12 mM proline, 750 mg/L carbenicillin and 50 mg/L paromomycin and cultured for 2 weeks at 27° C. Then the embryos were transferred to the same medium but containing higher level of selection agents (100 mg/L paromomycin) for 2 weeks before transferring these embryos to the medium containing 200 mg/L paromomycin for one or two more times of selection. Selected calli were brought to MS 6BA regeneration medium for about 2 weeks before moving them to MS OD medium in phytatrays and cultured in the lighting room. Plantlets with vigorous root and shoot development were selected and placed into soil and hardened off for 7 days before placement in the greenhouse.

Transgenic plants in the greenhouse were crossed with H99 and their immature embryos were harvested at 13 and 21 days after pollination for GUS staining (Table 2) and MUG (Table 3) activity assays. The GUS staining assays of transgenic plant tissues (Jefferson et al., EMBO J., 6:3901 (1987) provided a qualitative analysis of the corn embryo enhanced promoters of the present invention for determining the expression pattern in corn leaf, root, embryo, endosperm and seed coat tissues. GUS expression from the promoter sequences of the present invention was not detected in leaves and was infrequently detected in root tissues. GUS expression was detected in seeds, especially in the embryos of the seed. These promoters show enhanced expression in seed and seed associated tissues relative to expression in roots, leaves or other vegetative tissues.

TABLE 2

Qualitative GUS activity in transgenic corn tissue extracts

|  | Zm.700258061 pMON51008 | Zm.700267629 pMON51009 | Zm.700263624 pMON51010 |
|---|---|---|---|
| GUS activity in leaf | – | – | – |
| GUS activity in root | 15%+/85%–* | 18%+/82%–* | 16%+/84%–* |
| GUS activity in embryo | + | + | + |
| GUS activity in endosperm | part of aleuron + other part – | – | part of aleuron + other part – |
| GUS activity in seed coat | +/– | + | +/– |

+ got GUS activity
– no detectable GUS activity
+/– inconclusive or negative
*root tissue from some plants are positive The MUG assays provided a quantitative analysis of the embryo and endosperm expression in the transgenic seeds. Total protein was extracted from 10 embryos and 10 endosperms dissected from each half ear of a transgenic corn plant. The negative control PHxA/CK wild type corn tissue was assayed at the 13 dpp time point. The MUG assay used 500 µl of GUS extraction buffer added to the tissues, and tissues were ground with a teflon pestle in 1.5 ml eppendorf tube and centrifuged at 10 K RPM for 5 min at 4 degree (Beckman GS-15R). 400 µl of supernatant was transferred to a fresh 96-deep well plate. The extracts are frozen on dry ice and stored at –80 till use. The MUG assay consisted of generating a standard curve of activity with a serial dilution of 4-methyl umbelliferone (SIGMA M1381) from 31.2 pmoles to to 2000 pmoles. 5 µl of each extract was added to a flat bottom 96-well plate (Falcon 3872) in duplicate after the plant was preread for blanking the background. 200 µl of GUS assay solution (0.1M $KPO_4$ pH7.8, 1.0 mM EDTA, 5% glycerol, 10.0 mM DTT, 2 mM 4-methyl umbelliferyl glucuronide Fluka 69602) was added to each well and mixed with the samples by pipetting. The Plate was read kinetically on a F-max (Molecular Devices) at 37° C. with the filter pair: excitiation-355/emission-460. A typical read consists of 21 readings at 3 min intervals and last 1 hour. GUS activity (pmol/min/µg protein) was calculated base on MUG results and protein results of each sample. Total protein was assayed using Bio-Rad Protein Assay kit. Serial dilutions of BSA protein from 0.05 mg/ml to 0.5 mg/ml were used for the standard curve. 1.5 µl of extracts was added to flat bottom 96-well plate (Falcon) in duplicate. 200 µl of diluted dye reagent was added and mixed with the samples. The absorbance at 595 nm was measured in Spectromax 250 (Molecular Devices) at room temperature after 5 min incubation at room temperature. The MUG analysis demonstrated that the promoters isolated by the afore described invention express in corn seed tissue and differentially in embryo and endosperm tissues. Independent transformed corn lines can be selected from the population of plants transformed with the promoters of the present invention that express at different developmental stages of embryo and endosperm development in the seed.

TABLE 3

MUG assay/pmol/min/pg protein

| Construct | Promoter | Plant# | embryo/ 13dpp | endosperm/ 13dpp | embryo/ 21dpp | endosperm/ 21dpp |
|---|---|---|---|---|---|---|
| pMON51008 | 700258061 | s12811 | 50.4 | 0 | 0.3 | 0.1 |
|  |  | s12822 | 23.3 | 0 |  |  |
|  |  | s12823 | 0.4 | 0.1 | 8.6 | 0.3 |
|  |  | s12824 | 0 | 0 |  |  |
|  |  | s12829 | 2.7 | 0 | 19.1 | 0.6 |
|  |  | s12832 | 0.2 | 0 | 46.9 | 2.4 |
|  |  | s12834 | 9.8 | 0.3 |  |  |
|  |  | s12836 | 5.4 | 1.4 | 12 | 0.3 |
|  |  | s12826 | 0.9 | 0 | 210 | 0 |
|  |  | s12828 | 1.9 | 0 | 135.9 | 0 |
|  |  | s12833 | 6.6 | 0.2 | 135.5 | 132.9 |
|  |  | s12813 | 72.2 | 2.7 | 0.8 | 0.5 |
|  |  | s12835 | 6.7 | 0.2 | 66.2 | 1.8 |

TABLE 3-continued

| | | | MUG assay/pmol/min/pg protein | | | |
|---|---|---|---|---|---|---|
| Construct | Promoter | Plant# | embryo/ 13dpp | endosperm/ 13dpp | embryo/ 21dpp | endosperm/ 21dpp |
| pMON51009 | 700267629 | s13745 | 0 | | 1 | |
| | | s13746 | 0.9 | | 20.3 | 1.1 |
| | | s13747 | 0 | 0.2 | 0.7 | 0.9 |
| | | s13750 | 0 | 0.1 | | |
| | | s13752 | 0 | 0 | | |
| | | s13753 | 0 | 0 | | |
| | | s13754 | 0 | 0 | | |
| | | s13755 | 0 | 0 | 0 | 0 |
| | | s13756 | 0 | 0 | | |
| | | s13757 | 0.2 | 0.2 | | |
| | | s13759 | 1.6 | | 0 | 1.2 |
| | | s13760 | 0 | | 0 | 0 |
| | | s13761 | | 0 | | |
| | | s13763 | 0 | 0 | 0 | 0 |
| | | s13764 | 0 | 0 | | |
| | | s13766 | 0 | 0 | | |
| | | s13767 | 0 | 0 | | |
| | | s13768 | 0 | 0 | | |
| | | s13811 | | 0.6 | | |
| | | s13813 | | | 0 | 0 |
| | | s13814 | 0 | 1.4 | | |
| | | s13815 | 0 | 0.3 | | |
| | | s13816 | | | 0.7 | 0.6 |
| | | s13817 | 0 | 2.7 | | |
| | | s13818 | 0.8 | 0 | 5.2 | |
| | | s13819 | 3.8 | 0 | | |
| | | s13820 | | | 0.1 | 0.4 |
| | | s13821 | 0 | 0.1 | | |
| pMON51010 | 700263624 | s13769 | 0 | 0 | | |
| | | s13770 | 0 | 0 | | |
| | | s13771 | | | 0 | 0 |
| | | s13772 | 0 | 0 | | |
| | | s13773 | | | 5.6 | 0 |
| | | s13774 | 0 | 0 | | |
| | | s13775 | 0 | 0 | | |
| | | s13776 | | | 6.4 | |
| | | s13777 | 0 | 0 | 6.6 | |
| | | s13778 | 0 | 0 | | |
| | | s13779 | 0 | 0 | 27.3 | 1.8 |
| | | s13780 | 3.3 | 0 | | |
| | | s13781 | 0 | 0 | | |
| | | s13782 | 0 | 0 | | |
| | | s13783 | 0 | 0 | 5.4 | |
| | | s13785 | 0.5 | | 2.3 | 0 |
| | | s13786 | | | 3.6 | |
| | | s13789 | 0 | 0 | | |
| | | s13791 | 0 | 0 | | |
| | | s13792 | 2.8 | 0 | 23.4 | 0 |
| | | s13793 | 0 | 0 | 5 | |
| | | s13794 | 0 | 0 | 4.3 | |
| | | s13795 | | 0 | 3.8 | 0 |
| | | s13797 | 0 | 0 | 4.1 | 0 |
| | | s13799 | 0 | 0 | | |
| | | s13801 | 1.8 | 0 | 5.9 | |
| | | s13802 | 0 | 0 | 47.5 | 6.1 |
| | | s13805 | 0 | 0 | 5.1 | |
| | | s13806 | 0 | 0 | | |
| | | s13807 | 0 | 0 | | |
| | | s13809 | 0 | 0 | | |
| | | s13810 | 0 | 0 | | |
| | | s13826 | 0 | 0 | | |
| | | s13827 | 0.4 | 0 | 5 | 0 |
| | | s13828 | 0 | 0 | 0.4 | 0 |
| | | PhxA/CK- | 0 | 0 | | |

A large number of transformation and regeneration systems and methods are available and well-known to those of skill in the art. The stably transformed plants and progeny are subsequently analyzed for expression of the gene in tissues of interest by any number of molecular, immunodiagnostic, biochemical, and/or field evaluation methods known to those of skill in the art.

Example 7

Cis acting regulatory elements necessary for proper promoter regulation can be identified by a number of means. In one method, deletion analysis is carried out to remove regions of the promoter and the resulting promoter fragments are assayed for promoter activity. DNA fragments are considered necessary for promoter regulation if the activity of the truncated promoter is altered compared to the original promoter fragment. Through this deletion analysis, small regions of DNA can be identified which are necessary for positive or negative regulation of transcription. Promoter sequence motifs can also be identified and novel promoters engineered to contain these cis elements for modulating expression of operably linked transcribable sequences. See for example U.S. Pat. No. 5,223,419, herein incorporated by reference in its entirety, U.S. Pat. No. 4,990,607 herein incorporated by reference in its entirety, and U.S. Pat. No. 5,097025 herein incorporated by reference in its entirety.

An alternative approach is to look for similar sequences between promoters with similar expression profiles. Promoters with overlapping patterns of activity can have common regulatory mechanisms. Several computer programs can be used to identify conserved, sequence motifs between promoters, including but not limited to MEME, SIGNAL SCAN, or GENE SCAN. These motifs can represent binding sites for transcriptions factors which act to regulate the promoters. Once the sequence motifs are identified, their function can be assayed. For example, the motif sequences can be deleted from the promoter to determine if the motif is necessary for proper promoter function. Alternatively, the motif can be added to a minimal promoter to test whether it is sufficient to activate transcription. Suspected negative regulatory elements can be tested for sufficiency by: adding to an active promoter and looking for a reduction in promoter activity. Some cis acting regulatory elements may require other elements to function. Therefore, multiple elements can be tested in various combinations by any number of methods known to those of skill in the art.

Once functional promoter elements have been identified, promoter elements can be modified at the nucleotide level to affect protein binding. The modifications can cause either higher or lower affinity binding which would affect the level of transcription from that promoter.

Promoter elements can act additively or synergistically to affect overall promoter activity. In this regard, promoter elements from different 5' regulatory regions can be placed in tandem to obtain a promoter with a different spectrum of expression or a greater level of expression. In addition, a promoter element can be multimerized to increase levels of expression specifically in the pattern affected by that promoter element.

The technical methods needed for constructing expression vectors containing the novel engineered 5' regulatory elements are known to those of skill in the art. The engineered promoters are tested in expression vectors and tested transiently by operably linking the novel promoters to a suitable reporter gene such as GUS and testing in a transient plant assay. The novel promoters are operably linked to one or more genes of interest and incorporated into a plant transformation vector along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired agronomic characteristic(s).

By following the methods disclosed herein those of skill in the art of plant molecular biology can isolate DNA promoter sequences that are capable of regulating transcription of an operably linked DNA sequence heterologous to the promoter sequences. These promoters are useful for enhanced expression of transgenes in plant seeds, plant embryogenic tissues and plant callus tissues relative to the expression levels these promoters can direct in other plant cells and tissues, such as roots and leaves. The DNA molecules that are the promoter sequences of the present invention comprise various cis acting elements that can be isolated and fused with DNA molecules of known promoter sequences to create a hybrid promoter sequence. These hybrid promoters will have expression patterns different from the known promoter sequences and the promoters sequences isolated by the methods of the present invention. Well known promoters that function in plants include, but are not limited to the cauliflower mosaic virus 35S and 19S promoters, figwort mosaic virus 35S promoter, sugarcane bacilliform virus promoter and other plant virus promoters, plant actin promoters such as the rice actin promoter and the Arabidopsis actin promoters, and plant ubiquitin promoters. These promoters have minimal sequences that have been identified to direct transcription in transgenic plant cells. These minimal sequences are components of the hybrid promoters with cis acting elements of the DNA molecules of the present invention.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application is specifically and individually indicated to be incorporated by reference.

We claim:

1. An isolated DNA molecule comprising a first polynucleotide selected from the group consisting of nucleotide sequences having at least 80% nucleotide sequence identity to any one of SEQ ID NO:36–45, wherein said polynucleotide confers expression to a second polynucleotide in transgenic plant, embryogenic tissue, plant callus tissue, or a plant seed.

2. The isolated DNA molecule of claim 1, further comprising the second polynucleotide molecule.

3. The isolated DNA molecule of claim 2, wherein the first polynucleotide is a hybrid promoter.

4. The isolated DNA molecule of claim 2, wherein the second polynucleotide is a minimal promoter sequence.

5. An isolated DNA construct comprising a polynucleotide selected from the group consisting of nucleotide sequences having at least 80% nucleotide sequence identify to any one of SEQ ID NO:36–45, wherein said polynucleotide is operably linked to a second polynucleotide encoding a protein of interest and a 3' non-translated region.

6. A transgenic plant or plant cell comprising the DNA construct of claim 5.

7. A transgenic plant of claim 6, wherein said plant is a monocot plant.

8. A method of making a transgenic plant comprising:
(i) introducing into a plant cell a DNA construct comprising
(a) a promoter comprising, a polynucleotide selected from the group consisting of nucleotide sequences having at least 80% nucleotide sequence identity to any one of SEQ ID NO:36–45, wherein the promoter is operably linked to
(b) a second polynucleotide encoding a protein of interest and
(c) a 3' non-translated region;
(ii) selecting said plant cell; and
(iii) regenerating said plant cell into a plant.

9. An isolated DNA molecule comprising a first polynucleotide selected from the group consisting of SEQ ID NOS:36–45.

10. The isolated DNA molecule of claim 9, further comprising a second polynucleotide molecule linked to said DNA molecule.

11. The isolated DNA molecule of claim 10, wherein the first polynucleotide confers expression of said second polynucleotide molecule in transgenic plant embryogenic tissue, or plant callus tissue, or a plant seed.

12. The isolated DNA molecule of claim 10, wherein the first polynucleotide is a hybrid promoter.

13. The isolated DNA molecule of claim 12, wherein the second polynucleotide is a minimal promoter sequence.

14. An isolated DNA construct comprising a polynucleotide selected from the group consisting of SEQ ID NOS:36–45, wherein said polynucleotide is operably linked to a second polynucleotide encoding a protein of interest and a 3' non-translated region.

15. A transgenic plant or plant cell comprising the DNA construct of claim 13.

16. A transgenic plant of claim 6, wherein said plant is a monocot plant.

17. The method of claim 8, wherein the promoter comprises a polynucleotide sequence selected from the group consisting of SEQ ID NO:36–45.

* * * * *

SEQUENCE LISTING

<160> NUMBER OF SEQ ID NOS: 51

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1
gtaatacgac tcactatagg gc                                            22

```
<210> SEQ ID NO 2
<211> LENGTH: 19
<212> TYPE: DNA
<213> ORGANISM: Artificial sequence
<220> FEATURE:
<223> OTHER INFORMATION: Primer

<400> SEQUENCE: 2
actatagggc acgcgtggt                                              19

<210> SEQ ID NO 3
<211> LENGTH: 30
<212> TYPE: DNA
<213> ORGANISM: Artificial sequence
<220> FEATURE:
<223> OTHER INFORMATION: Primer

<400> SEQUENCE: 3
agggcaagct tggtcgacgg cccgggctgg                                  30

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4
cggcagggtt ttcccagtca cga                                         23

<210> SEQ ID NO 5
<211> LENGTH: 24
<212> TYPE: DNA
<213> ORGANISM: Artificial sequence
<220> FEATURE:
<223> OTHER INFORMATION: Primer

<400> SEQUENCE: 5
agcggataac aatttcacac agga                                        24

<210> SEQ ID NO 6
<211> LENGTH: 27
<212> TYPE: DNA
<213> ORGANISM: Artificial sequence
<220> FEATURE:
<223> OTHER INFORMATION: Primer

<400> SEQUENCE: 6
cagaaagcct ccattcctta tcaggca                                     27

<210> SEQ ID NO 7
<211> LENGTH: 27
<212> TYPE: DNA
<213> ORGANISM: Artificial sequence
<220> FEATURE:
<223> OTHER INFORMATION: Primer

<400> SEQUENCE: 7
cgagaggaag tgcctggcgt aatcaaa                                     27

<210> SEQ ID NO 8
<211> LENGTH: 26
<212> TYPE: DNA
<213> ORGANISM: Artificial sequence
<220> FEATURE:
<223> OTHER INFORMATION: Primer
```

<400> SEQUENCE: 8
gctcatcaga gttgccgtcg ttgcta                                                                26

<210> SEQ ID NO 9
<211> LENGTH: 44
<212> TYPE: DNA
<213> ORGANISM: Artificial sequence
<220> FEATURE:
<223> OTHER INFORMATION: Primer

<400> SEQUENCE: 9
cgcggatcca gatctactcg tctgacccat ccgttatcac tccg                             44

<210> SEQ ID NO 10
<211> LENGTH: 26
<212> TYPE: DNA
<213> ORGANISM: Artificial sequence
<220> FEATURE:
<223> OTHER INFORMATION: Primer

<400> SEQUENCE: 10
agtgaggcga tccattcacg cgccta                                                                26

<210> SEQ ID NO 11
<211> LENGTH: 26
<212> TYPE: DNA
<213> ORGANISM: Artificial sequence
<220> FEATURE:
<223> OTHER INFORMATION: Primer

<400> SEQUENCE: 11
gatcgcttgc actctctgcc tctctg                                                                26

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
tctccccgca aggcgcgtat ctgatga                                                               27

<210> SEQ ID NO 13
<211> LENGTH: 42
<212> TYPE: DNA
<213> ORGANISM: Artificial sequence
<220> FEATURE:
<223> OTHER INFORMATION: Primer

<400> SEQUENCE: 13
cgcggatcca gatctggcgc gtcggggcac cggccggcgc ag                                  42

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14
ttgccgaccc ctccttcacc ttctcct                                                               27

<210> SEQ ID NO 15
<211> LENGTH: 27

```
<212> TYPE: DNA
<213> ORGANISM: Artificial sequence
<220> FEATURE:
<223> OTHER INFORMATION: Primer

<400> SEQUENCE: 15
tgtccttcgc cttcaccttc gctgtct                                        27

<210> SEQ ID NO 16
<211> LENGTH: 26
<212> TYPE: DNA
<213> ORGANISM: Artificial sequence
<220> FEATURE:
<223> OTHER INFORMATION: Primer

<400> SEQUENCE: 16
ggaatctcca cgttctggca cgacga                                         26

<210> SEQ ID NO 17
<211> LENGTH: 26
<212> TYPE: DNA
<213> ORGANISM: Artificial sequence
<220> FEATURE:
<223> OTHER INFORMATION: Primer

<400> SEQUENCE: 17
tgtctctcgc aaagtcgcaa tgtctg                                         26

<210> SEQ ID NO 18
<211> LENGTH: 28
<212> TYPE: DNA
<213> ORGANISM: Artificial sequence
<220> FEATURE:
<223> OTHER INFORMATION: Primer

<400> SEQUENCE: 18
tgaggctgga cggtttgatc tcccactt                                       28

<210> SEQ ID NO 19
<211> LENGTH: 42
<212> TYPE: DNA
<213> ORGANISM: Artificial sequence
<220> FEATURE:
<223> OTHER INFORMATION: Primer

<400> SEQUENCE: 19
cgcggatcca gatctgaaga agaagaaccc gagtcgccac cc                        42

<210> SEQ ID NO 20
<211> LENGTH: 29
<212> TYPE: DNA
<213> ORGANISM: Artificial sequence
<220> FEATURE:
<223> OTHER INFORMATION: Primer

<400> SEQUENCE: 20
agctctcgat gaacatcttg cctttcctc                                      29

<210> SEQ ID NO 21
<211> LENGTH: 43
<212> TYPE: DNA
<213> ORGANISM: Artificial sequence
<220> FEATURE:
<223> OTHER INFORMATION: Primer

<400> SEQUENCE: 21
```

-continued cgcggatcca gatctgaatg gaatgcgaag cgaggtagcg agc   43

<210> SEQ ID NO 22
<211> LENGTH: 29
<212> TYPE: DNA
<213> ORGANISM: Artificial sequence
<220> FEATURE:
<223> OTHER INFORMATION: Primer

<400> SEQUENCE: 22
acgacacctc tcgccatagc aaactctcc   29

<210> SEQ ID NO 23
<211> LENGTH: 44
<212> TYPE: DNA
<213> ORGANISM: Artificial sequence
<220> FEATURE:
<223> OTHER INFORMATION: Primer

<400> SEQUENCE: 23
cgcggatcca gatctcattc atctgatcca tccgtcacca ctcc   44

<210> SEQ ID NO 24
<211> LENGTH: 27
<212> TYPE: DNA
<213> ORGANISM: Artificial sequence
<220> FEATURE:
<223> OTHER INFORMATION: Primer

<400> SEQUENCE: 24
ggagatgtgg ttgagcgcca tcatcgg   27

<210> SEQ ID NO 25
<211> LENGTH: 27
<212> TYPE: DNA
<213> ORGANISM: Artificial sequence
<220> FEATURE:
<223> OTHER INFORMATION: Primer

<400> SEQUENCE: 25
agtctcagtc ctggcctctt tggggtg   27

<210> SEQ ID NO 26
<211> LENGTH: 30
<212> TYPE: DNA
<213> ORGANISM: Artificial sequence
<220> FEATURE:
<223> OTHER INFORMATION: Primer

<400> SEQUENCE: 26
caaatcactc ggagaaagaa atatgcttgg   30

<210> SEQ ID NO 27
<211> LENGTH: 29
<212> TYPE: DNA
<213> ORGANISM: Artificial sequence
<220> FEATURE:
<223> OTHER INFORMATION: Primer

<400> SEQUENCE: 27
ggctactact gactgtgacg atggtgctc   29

<210> SEQ ID NO 28
<211> LENGTH: 27
<212> TYPE: DNA
<213> ORGANISM: Artificial sequence

```
<220> FEATURE:
<223> OTHER INFORMATION: Primer

<400> SEQUENCE: 28
ccagaagcag gaggaggacg aagaagg                                27

<210> SEQ ID NO 29
<211> LENGTH: 26
<212> TYPE: DNA
<213> ORGANISM: Artificial sequence
<220> FEATURE:
<223> OTHER INFORMATION: Primer

<400> SEQUENCE: 29
gaaacgaact ccagagcttg ccgagg                                 26

<210> SEQ ID NO 30
<211> LENGTH: 27
<212> TYPE: DNA
<213> ORGANISM: Artificial sequence
<220> FEATURE:
<223> OTHER INFORMATION: Primer

<400> SEQUENCE: 30
acaagacgat tcccagacaa gggacca                                27

<210> SEQ ID NO 31
<211> LENGTH: 26
<212> TYPE: DNA
<213> ORGANISM: Artificial sequence
<220> FEATURE:
<223> OTHER INFORMATION: Primer

<400> SEQUENCE: 31
gcccacacct cacggcatcc atattt                                 26

<210> SEQ ID NO 32
<211> LENGTH: 29
<212> TYPE: DNA
<213> ORGANISM: Artificial sequence
<220> FEATURE:
<223> OTHER INFORMATION: Primer

<400> SEQUENCE: 32
acgagcgcca cttgtcttga acttgttgg                              29

<210> SEQ ID NO 33
<211> LENGTH: 41
<212> TYPE: DNA
<213> ORGANISM: Artificial sequence
<220> FEATURE:
<223> OTHER INFORMATION: Primer

<400> SEQUENCE: 33
cgcggatcca gatctagcgc gaactgccgg cggcgctgct c                41

<210> SEQ ID NO 34
<211> LENGTH: 27
<212> TYPE: DNA
<213> ORGANISM: Artificial sequence
<220> FEATURE:
<223> OTHER INFORMATION: Primer

<400> SEQUENCE: 34
gtcggttaga ccgaacaaaa attcagc                                27
```

```
<210> SEQ ID NO 35
<211> LENGTH: 43
<212> TYPE: DNA
<213> ORGANISM: Artificial sequence
<220> FEATURE:
<223> OTHER INFORMATION: Primer

<400> SEQUENCE: 35
cgcggatcca gatctgtcgg ttagaccgaa caaaaattca gcc         43

<210> SEQ ID NO 36
<211> LENGTH: 654
<212> TYPE: DNA
<213> ORGANISM: Zea Mays

<400> SEQUENCE: 36
ctgcccatcg tcgcgcgccg gaggcccgac ggccgaggat ggtccttcgt gtgggacgac     60
gactcgytty tgctccagct ccgcgacggc attcccgagg atatggaggt gytcttcgtc    120
ggytccctcc gcgccgatgt ccccgtagcg agcaggacg  aggtgtcgca ggcgttgctc    180
gaccggttcc gytgcgcgcc ggtcttcctc cctgaccgcc tcaacgaccg cttctaccac    240
ggcttctgca agcgccaact ctggcctctg ttccactaca tgctcccctt ctcctcatcc    300
gcgtccgccg ccggcaccac ctcttcctcc tccgccgcca cttgcaacgg tcgcttcgac    360
cgcagcgctt gggaggcgta cgtgctcgcc aacaagttct tcttcgagaa ggtcgtcgag    420
gtaatcaacc cggaggatga ctacgtttgg gttcacgact accatctcat ggcgctgcct    480
accttcctcc gccgctgctt caaccgcctc cgcatcggat tcttcctcca cakccccttc    540
ccctcgtccg agatctaccg caccctccct gttcgggagg agatactcaa ggcgctgctc    600
aactgtgacc taattggctt ccacactttt gattacgcca ggcacttcct ctcg          654

<210> SEQ ID NO 37
<211> LENGTH: 277
<212> TYPE: DNA
<213> ORGANISM: Zea Mays

<400> SEQUENCE: 37
ctgggacgac ggttcgtgag cgactttccc atatacgatg ccgtggctc  cggcgcccgc     60 ctcgtcgctc gcttgcaggg agtcactgtc caaatcggca gctcgcacta gctagtcagc    120
atcgtcttcg aggccgagag gtagttaaat gtatgcatgc atgcatgtag tatatatata    180
atgcatgtgc gattcattca ttggttcatc gtcgtctgca ggcttaaggg ctccacgctg    240
ctcaccaacg gagtgataac ggatgggtca gacgagt                             277

<210> SEQ ID NO 38
<211> LENGTH: 476
<212> TYPE: DNA
<213> ORGANISM: Zea Mays

<400> SEQUENCE: 38
aaaaaatata gtttctaaac tagcccttag aagatactta aataagtatt gtttcttatt     60
tttacgggat gctatgcgga ggggtctact acacatattt actatctcat ctcccatttt    120
attctatatt atatatatat aaatttgcaa acattgttat acatcgtcat ttccagtgag    180
acacagcggt cgtgtcatca gaaaagcgga cacgcgtcgc gtcgcgaggc caggtgggtt    240
atgcacggac ctgctatgct agccatgctc aggctccact ctccacccgt ccaccgactt    300
ctcttctcaa cgagactgcg tcctcaccat gcacgacgac acgtgcgatg ccatcacaca    360
```

```
tccacactca cctgttgcct ctatatccac cgccccaccg ccgtagcacc agaaagaaat    420
gtacagtcta cagtctacac acaagctgac cagagaggca gagagtgcaa gcgatc        476
```

<210> SEQ ID NO 39
<211> LENGTH: 344
<212> TYPE: DNA
<213> ORGANISM: Zea Mays

<400> SEQUENCE: 39

```
atcaggttag actaacttcc tttctctgtt atgcatatgc atgtgtgtat gccttttgat     60
ttcttggtat gatggaataa tcaggggtgg atctgcaccc tgaaccaccc tgtcgtggcc    120
cagggtttga tccatgtaat cctttataag tctatttaat ccagtataaa atgacttaga   180
taaaaggtag agaagaaaat ttagtgccga gctaccaagg caccttcttt attccgtcct   240
tgctcagtca cacctcgctc tcgctcactc tcgccgtccg cacagccgct catcgtctcc   300
cactgcctgc cctctccctg cgccggccgg tgccccgacg cgcc                    344
```

<210> SEQ ID NO 40
<211> LENGTH: 547
<212> TYPE: DNA
<213> ORGANISM: Zea Mays

<400> SEQUENCE: 40

```
aaaaattttt tagtctaaac gtgattttac ttctgtttaa gtttaagggc taaawtaaaa     60
aaaaattcgg cagaagaaac tacgcgcgga cagagaaata cgatcggcca agccgtatac   120
ggagacgtgg cgtgatcctc tcagcacagc attccctagg tggtggtgat gtctgccttc   180
accactatca gatttgcaca cgcagccacg caggacatct gctacagggc acgcggcggc   240
tcagaacgaa gctacgagca cagcgaggtc gccacctcac ggtgcgacgt gcagctccag   300
ctgctcaccg accactgcat gtcgcccacg taagattcaa ccagtccgcc actccaagat   360
ccaagactcc agagaccggc cggcctggcc gctagctttt atatacttcc ggcagccatg   420
caccctcatg tccagcatat cgacgcagag tcgcagtcgc agcacacact gaattctctt   480
tagctagcta agagarggta gccacaccaa gacaggatgc agacarcgaa ggtgaaggcg   540
aaggaca                                                              547
```

<210> SEQ ID NO 41
<211> LENGTH: 856
<212> TYPE: DNA
<213> ORGANISM: Zea Mays

<400> SEQUENCE: 41

```
actttagtta gggttcggtc tttaattctt ttgctgggca gcagtaaacg gagatgagaa     60
gcgcgagctg atcattgttg ccattctgtg caacgaagct aggggaccaa tgctgactcg   120
cacgagggca tagttgctga tggtcataga cgacgcgttc acttaaaata ataaagaatt   180
ataaattgtt gtcataagtc gtgcagccta atataggaga gtgcggcatt gctgtagcta   240
attaagagag tattccggtc atgcttgagc ttggagaatt tttgaggscc cgttcgcttg   300
gagagtcgga gatttttgag ggcccgtttc gcttgcacaa tawtaaacaa agatttgttc   360
tagctcatcc aaatctatat aaattaaaga agtaattcgg ttaggaatca atccaagagc   420
tctaattctt aaaaaccgaa cagggcctga gttgtttgtc tagacgacat tatctgatta   480
agttattttc atcttcaatt tcaaatgtga tctarcagca taaaacttgt tgtctgacag   540
```

-continued

| | | |
|---|---|---|
| atatttgact tccacacggg ccacagctca attacaaaca tacttcaaac atcaggcaga | 600 | |
| ggcagagcac tagcagcatt cgctacgtgg cggtgggcag cagtggccag cacattcgac | 660 | |
| aactgccacg gatcccgtac tacttcaaac acgtatcgct tccagaatcc agagtcacac | 720 | |
| gtgtgcagct gcatgaaccc agctcactcc cttaagaaca gctcgacgct cacctgtcta | 780 | |
| gtctagctcg tgcatgccgc cctgagcgcc actgcacaga cgcgcagaga cagacattgc | 840 | |
| gactttgcga gagaca | 856 | |

<210> SEQ ID NO 42
<211> LENGTH: 1137
<212> TYPE: DNA
<213> ORGANISM: Zea Mays

<400> SEQUENCE: 42

| | | |
|---|---|---|
| ctgcacggat gcggccgagt gcggcagcac agcagcgcgc gcgcgctcca catcgccttc | 60 | |
| gctagttcgc tccgccacgt acgcggcccg gcctccacct ggcggcgcgc atggctgcga | 120 | |
| ccctcgccgc gccacctctt catatacgct gcagctcgcc tcgaaccctc gcatcgaacg | 180 | |
| cacactcgca ctcgcacgta caccacacta gttaccacag acgacgggcg ccatgaaagt | 240 | |
| cccggtgctt cttctcctgg tctccctgtg cttctcgctc gcgctcgcgt ggcaaacgga | 300 | |
| cacggaatcg ggctcaggca ggccgtacca ctacggcgag gagagtttcc ggcactggac | 360 | |
| gcgctcccgg cagggccggt tcagggtgct ggaacggttc acccacgagc tgctggagga | 420 | |
| cgccgtcggc aactaccgcg tcgccgagct ggaggccgcg ccgcgcgcgt tcctgcagcc | 480 | |
| cagccactac gatgccgacg aggtgatgtt cgtgaaggaa ggcgagggcg tcatcgtgct | 540 | |
| gctccgcggc gggaagaggg agtcgttctg cgtcaggag ggcgacgtca tggtcatccc | 600 | |
| cgcgggcgcc gtcgtgtact cggccaacac gcaccagtcg gagtggttcc gcgtcgtctt | 660 | |
| gctcctcagc cccgtcgtct ccacgtctgg acgcttcgag gttcgctttg cttctcgtgc | 720 | |
| tttaatcttg catgcaaata gatggaggtg acggaaactt ctgttctctt cgtgatttcg | 780 | |
| gcaggagttc ttccccatcg gaggcgagag ccccgagtcc ttcctcagcg tcttcagcga | 840 | |
| cgacgttatc caggcgtcgt tcaacgtatg catgcccttc atcgtcctca ggccgggtt | 900 | |
| tcttctctta tacatcgatt tttcgctagc tagctagcaa actaacccag atttgaacac | 960 | |
| gaccatgcat gtgtcctaga ctcgccggga ggagtgggag aaagtgttcg agaagcagag | 1020 | |
| caagggggag atcacgacgg cgtccgagga acagatccgg gagctgagca ggtcctgctc | 1080 | |
| acgtggtggc cgcagcagcc gcagcgaggg tggcgactcg ggttcttctt cttcaga | 1137 | |

<210> SEQ ID NO 43
<211> LENGTH: 753
<212> TYPE: DNA
<213> ORGANISM: Zea mays

<400> SEQUENCE: 43

| | | |
|---|---|---|
| atcactacag tttataatgc ttcagttttc gaatactaca atatccaata cataaaggtg | 60 | |
| tttgggaaaa actttggttg agaccaatca gccagagcgg gaccaagctg tcgctctctt | 120 | |
| tacagagaaa aactttggtg agaccaaagt tttcaaaact gcaaacaag tacagtattt | 180 | |
| acaatattat agtttagtat acagaaattt cagataaatt ttcaaacacc tcaaaatata | 240 | |
| taataccaca gtattactca atactataat attactataa tactacagaa aaactttgtt | 300 | |
| ctcaaacacc tcttccatcg gtatgtcctc cgtcatccc aaagccttca ttcggctcgc | 360 | |
| tgtcttcttt ctatcgctca caacacaacc atagcccaca ggccgccggc ggccgccagc | 420 | |

| | |
|---|---|
| cgacgtcctc ccatttcgct cccctcctc cgctgcggtc gagcaaaagt tccggccatc | 480 |
| cggcaatccc cccgcacccg gcggttcaaa ccgtatcttt ctgacctgac gcggctacga | 540 |
| cgtcgctcct ccggtcccct cgatccggtg gggtccgttt ctttcaagcg cggcctcgct | 600 |
| ggccgcctcg tggcagtgac cgtcgaaccc tctataaatc ccgtgccccg agcacccttc | 660 |
| ctcgatcaca caacccaaag cagccacagc agcctccttc ctcctctcac tctcgctcgc | 720 |
| gctgcgctcg ctacctcgct tcgcattcca ttc | 753 |

<210> SEQ ID NO 44
<211> LENGTH: 684
<212> TYPE: DNA
<213> ORGANISM: Zea Mays

<400> SEQUENCE: 44

| | |
|---|---|
| gtgttgtcca aactggacat cagacaagca cgacaatgac aggcgttcgc caagtgtacg | 60 |
| tacaggagac gaaacacgaca agtagcaccg tcctggccga gagcccgtca tgctcatgca | 120 |
| tgcatgctga tcatctcgat aaatatacag cagagagctg agctacgtac acaaacaaga | 180 |
| agcttgcatt gttcgtttgc tcgatcgttg cagataatgg agaaccctgc tccgagtatc | 240 |
| gtagcgcccc ccattgccgc acctgtatca gcgaacttca gcagactcgc cttccgcaac | 300 |
| ctgtacatcc gacggacggg tccagacagc agggagatgg tgactgtgga gggaagaaga | 360 |
| ggctctagtg atcagacagg cgacatgagg tacgtgagtg acttcccgt ctacgatggc | 420 |
| cgtggctccg acgccgtcct ggtggctcgc gtgcagggcg tcacaaccac gttcgggaac | 480 |
| tccaaccagt tcttcaccgt cgccttcgag gccggcaggt tcttcgttta gacagatata | 540 |
| tagctagata gatgctagct tgtggttcat atatagcaga tagatatatg catccgccat | 600 |
| tgatcgtcca tcgtcatcga tcagcaggct caagggctcc acgctcctta ccgaaggagt | 660 |
| ggtgacggat ggatcagatg aatg | 684 |

<210> SEQ ID NO 45
<211> LENGTH: 1025
<212> TYPE: DNA
<213> ORGANISM: Zea Mays

<400> SEQUENCE: 45

| | |
|---|---|
| actccgtact tctaaagggt gggttatta tgtacatggt ccttgcgtta cggagtttga | 60 |
| ataaacaaaa acaaaaaaat atatagatga ataaacaaat cagtcacaaa aacaaaaaaa | 120 |
| atctagatga gaaataaatc tggacggaca aatcagcaac ataaacaaaa aatatggaca | 180 |
| acaaaaaaca aatttgtgac aaagacaaaa aagaaaacta ttaaacgccc accatgagac | 240 |
| ttgaacccac aacctcaagg ttaaaaacct tatactctac cgactaagct agatgagttt | 300 |
| tgtcattaca tattcgagct cggcggcata gatcttggcg ccgagctcgg tgccacgttg | 360 |
| gcgccacgtc gtctaggttg tgccagcgca acacgttctt cggcgtcata gcctatggcg | 420 |
| ccgagatgtg ttacctcggc gctataggct atgacgccga gtaaagggtc caaagtgac | 480 |
| attaaaattt tttaaggtct aaacgtgaat ttttttcaga gaaacggaca aaatacaaaa | 540 |
| agttcgggcg catgcatggg tgggtgacg gtggcgctcg caactcagta actcacacgt | 600 |
| gcccgctcgg actcaagggg ctggggcacg ggcatgggca tgggcgcatg gcatgcctgc | 660 |
| aagcagagtg tagcagacgg cgtcagcacg ccaccttggc cgcttggcgg ccacacggtg | 720 |
| ccgacctgac aggggcgcgc gctctcgagt cccagtccca ggctactgcc gtggcgggcc | 780 |

```
ttacggccgc cacgtcggcc gaggccaccc atccatgcaa gcggcgcatg ggaacgtggc      840
attccggcgc gacggcacga ccgcgctccc gcgccatgcg tcacggtcac gtgcacgcag      900
agccccgctc gccttctata ggtagcgccg cgcgggtggc gtcgcttctg gtctgtggcg      960
gatcggatcg acacccagcc agcgcgtgga gagtagaaca ccccaaagag gccaggactg     1020
agact                                                                 1025
```

<210> SEQ ID NO 46
<211> LENGTH: 910
<212> TYPE: DNA
<213> ORGANISM: Zea Mays

<400> SEQUENCE: 46

```
aaatttgtgc ccttagtttt agtggtgtgc tcacatataa cctcagtcgt gttttttttct     60
cagctgtgct cacatacgag cacgtacaat gagactgaca aacgagcgtg aatgggtagg     120
gagttttgtt ggagatacga ataattacac aaatcgtata aaatacggat gctaagttta     180
atagggtgat tgttaaagtt ggtctaagtg gataaagcag ctcaatagta gaaccgaggc     240
aaccccggtg aagaaaacaa gcgctcgata agcgcatgta tgggcatggg tgcaccgtgc     300
atgtccaggc cacctggagc tcgctcgcgc gtattgctcc actccaccgc atcaccacca     360
ccaagtggca tgcatatcga gcagagggaa accacatcca acttgtactc gatcgccact     420
gtcgacattt ccctatcgtc cgtctgaacc gatcaacagg tgatgagatc gatcgtgatc     480
gtcatctggt accgttcgtg caccatcgcg tcgagacgag agcaacgcac tcgatttgta     540
ctccactact agttcttccg gccggcctac gggttctctc tcaaacgtgg cgagtgcctt     600
gcacatggtg gtggtccggt gaccagctga ccgacgccta tgggcgtgcg cgcgcgcgaa     660
tcagctccat cgacatgggc aggcttcgcg aaggtacgga cctcgtgaca caacacagcg     720
cgtggcgtgt cctttctacg tggccgtcat gtgggaggct gggagcccgg ccacgctacg     780
tggcccgggg actgcctcgc tgctgctgct tataaatatt cccgctgga aaagccccca      840
gccatcatca gtagctagct gttcgaagct ttcagccgat cgagcaccat cgtcacagtc     900
agtagtagcc                                                            910
```

<210> SEQ ID NO 47
<211> LENGTH: 734
<212> TYPE: DNA
<213> ORGANISM: Zea Mays

<400> SEQUENCE: 47

```
actcggcaaa gagaccgctg gcgatgtaca gttcgccgaa cgttctttgc caagtgttac      60
actcggcaaa tcttttgccg agtgtaaaat arcctttgcc gagtgtctga gacacatggc     120
aaaggagctg attccggtag tgatgtatta cttgtgatca ttttggagat gaagagaggc     180
cactaatgct tcatttttgaa tgtttgtgtc actatttgtt tttcttcagc ttcatttttga    240
tccgattcaa aaagaaaagt tttatttttga taaaactcta acatttttgta ttttttgtttg    300
tctaatgtgc agttgaagaa gcgcatgavc cgkttaagag gaagcstaga aagatgaggc     360
agargtcaag tacacatcga gggagatyca wggrgtgtcc ccgccarccc ttgcsttgga     420
ttgccytgcy ggkgtagtac aaacagtttc attttccytt gcgtggtckt gggcccamam    480
cgtcgtcstg twtaacmaag cggctcawkc araccaacac gcggsgartc ccarcgctty    540
camagcawta mcgccgccyc ytycamatka rgsktyaatt caargsgccc aatgcaactc    600
ccttttctct tgtccctgtc ctttccgcaa cagagcttgt gagcttgacc agcgagaggc    660
```

```
gagtggctag gacctaggcc tccgatccat gcaggtccct gtgggtttcc tcggcaagct    720
ctggagttcg tttc                                                      734
```

<210> SEQ ID NO 48
<211> LENGTH: 1129
<212> TYPE: DNA
<213> ORGANISM: Zea Mays
<220> FEATURE:
<221> NAME/KEY: misc_feature
<222> LOCATION: (1)..(1129)
<223> OTHER INFORMATION: N = any nucleotide

<400> SEQUENCE: 48

```
cctctttcct ttagaggggg aatacaatta tatgtcttgc ttaccttcaa tgcttgctga      60
atcaagatct ctgtaatgtg ctaccatgct attttaactt aggggacagt atgatccagc     120
cttatgggct ggcaaagtgg gcaatagttg gcgtacaact gacgacataa cggatacatg     180
gaaaaggtaa cccatgttct tttcagagga aaaagagat agaacattag ctctgtcgat      240
gtgctctcaa actgacttat ttatgtatct ggtgaaaaca agcatgacag acattgctga     300
taagaacaac aagtgggcat catatgctgg acctggtggt tggaatggta attatgttag     360
tgatgagttc aagctgtctg caatttgctg tgctttgtgg agctgttcag tatactgtta     420
ctctgttatt gaacctctgc ttttctgcag acccagatat gctggaagta ggcaatggtg     480
acatgacctt aacagagtat cggctcacat tttagcatat gggytctcat gaaggtaagt     540
tttcactgar aattggaccc gatgttgtat gktcatattt tgagtaagga ggttcgacca    600
angagttttg aaaattaaaa actgtagttc attgaagatg atggttggca tgtaagtatt     660
acagttattg attctccact tactgatgtt acatttggat gcgagaaagg agatatccta     720
ctcntaatgg gttaactgct acctatata ctgttgtgct tcaggcccct ctattaattg     780
gctgtgatgt cagaaacatg acttctgaaa caatggaaat actgagcaac aaagaagtaa    840
ttcaagtaaa ccaaggtatt attctgattc ttctttcgga gagaacatgt tatcctggtt    900
tagtatcaca ggctacaaaa atatgttttt acatagaaac tgacaacctt cttatttttg    960
tatataattt cccaacatat cttatatggc agaacaattt aaattcgtaa tgctcatata   1020
atcacataaa ctcttgagtt gcatgtgttt tattttctgc agatcctctt ggagttcaag   1080
gaagaaaaat tttaggacaa ggaaaatatg gatgccgtga ggtgtgggc                1129
```

<210> SEQ ID NO 49
<211> LENGTH: 571
<212> TYPE: DNA
<213> ORGANISM: Zea Mays
<220> FEATURE:
<221> NAME/KEY: misc_feature
<222> LOCATION: (1)..(571)
<223> OTHER INFORMATION: N = any nucleotide

<400> SEQUENCE: 49

```
tnacagaatg atcaaantgg attttgnatt gatcaagggg gnaagtgttn caattttttt      60
gttgaccaat ccaaggggc tcgacgaaat acattcctaa agggacacac ccctagggca     120
agcttggtcg acgcccggg ctggtataag tctgtcttcc ctgcaataaa gcaatacaa      180 cttgccattc tctcgagtct cgttttcact gcgctttaac aagagctaaa aagtgcgaga    240
ccgcgagaga aatccagcag gtgtacgtac gtaaagcgag agtcgacgcg tgggcgcggc    300
agacgcgagc ctcccgccac gttggcctcg ttcccgcgcc acgcggccac gcctgcctgc    360
```

-continued

```
ctcctcacct tgtttatatg cctcgcgcct ccctcaccgt gccaatgcca tgcgcgcgct      420
actgcatctg cggctcatca atccgtgcag tcccagagca ccccgtcttc ccgctactcc      480
cgcaagggcg ctcgtcgctt ccttctccgg ggcgtggcag gcaccttctg gtagagcgag      540
agcgagagca gcgccgccgg cagttcgcgc t                                     571
```

<210> SEQ ID NO 50
<211> LENGTH: 579
<212> TYPE: DNA
<213> ORGANISM: Zea mays

<400> SEQUENCE: 50

```
aaatattaga tactactgat aaaaaagata aacaccatta gctatattac caccctctcc       60
aactgttttc tgaactaatt gtaaatgggc ccatagtgta gtcgtcaagc atggaggccc      120
gctcgaccga cctcctcgat cgctcaaatt tggaaacagc ggttgctact gaccggggtg      180
agtgctgcgt tgttggcgac tgccctgttt tttaatggat tcagtgagag ctaaaaagtg      240
cgagactgcg agagaaatcc agcaggtgta cgtacgtaaa gcgagagtcg acgcgtgggc      300
gcggcagacg cgagcctccc gccacgttgg cctcgttccc gcgccacgcg gccacgcctg      360
cctgctccta ccttgtttat atgcctcgcg cctcctcacc gtgccaatgc catgcgcgcg      420
ctactgcatc tgcggctcat caatccgtgc agtcccagar cacccgtct tcccgctact      480 cccgcaaggg cgctcgtcgc tttccttctt ccggggcgtg gcaaggcacc tttttggtaa      540
aagcgagagc caagagcagc gccgccggca gttcgcgct                             579
```

<210> SEQ ID NO 51
<211> LENGTH: 193
<212> TYPE: DNA
<213> ORGANISM: Zea Mays

<400> SEQUENCE: 51

```
ctgtttcagg catatctgcc acctcggtca catgccgtcc gccacgtcga gaccgcgagc       60
tccatacgtg tcacgcgcag ccattcccga cgtctccggt gccgtgtttt aaagaacgcg      120
ccgtagcgca gcgcactgcg ccactcatct gatgccgtaa cacaaggctg aattttttgtt      180 cggtctaacc gac                                                         193
```